US008968738B2

(12) United States Patent
Mitre et al.

(10) Patent No.: US 8,968,738 B2
(45) Date of Patent: Mar. 3, 2015

(54) METHODS OF TREATING AUTOIMMUNE DISEASES WITH ANTI-FCεRI ANTIBODIES

(75) Inventors: Edward E. Mitre, Rockville, MD (US); Marc P. Hübner, Nordrheinwestfalen (DE)

(73) Assignee: The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 113 days.

(21) Appl. No.: 13/821,961

(22) PCT Filed: Sep. 14, 2011

(86) PCT No.: PCT/US2011/051518
§ 371 (c)(1),
(2), (4) Date: Mar. 8, 2013

(87) PCT Pub. No.: WO2012/037196
PCT Pub. Date: Mar. 22, 2012

(65) Prior Publication Data
US 2013/0171137 A1  Jul. 4, 2013

Related U.S. Application Data

(60) Provisional application No. 61/382,541, filed on Sep. 14, 2010.

(51) Int. Cl.
A61K 39/395 (2006.01)
C07K 16/28 (2006.01)
A61K 39/00 (2006.01)

(52) U.S. Cl.
CPC ....... A61K 39/3955 (2013.01); A61K 2039/505 (2013.01); A61K 2039/545 (2013.01); C07K 16/283 (2013.01); Y10S 424/805 (2013.01); Y10S 424/81 (2013.01)
USPC .................. 424/144.1; 424/133.1; 424/139.1; 424/153.1; 424/805; 424/810

(58) Field of Classification Search
None
See application file for complete search history.

(56) References Cited

U.S. PATENT DOCUMENTS

| | | | | |
|---|---|---|---|---|
| 6,165,799 | A * | 12/2000 | Kinet | 436/507 |
| 7,384,633 | B2 * | 6/2008 | Sugimura et al. | 424/142.1 |
| 7,655,299 | B2 * | 2/2010 | Morita et al. | 428/325 |
| 2002/0183299 | A1 | 12/2002 | Voskuhl et al. | |
| 2003/0064063 | A1 | 4/2003 | Saxon | |
| 2007/0135621 | A1 | 6/2007 | Bourel et al. | |

OTHER PUBLICATIONS

Fiebiger et al., J Clin Invest. Jan. 1, 1998;101(1):243-51.*
Marone et al., Clin Exp Allergy. Jan. 1999;29(1):17-27.*
Sun et al., J Int Med Res. Nov.-Dec. 2008;36(6):1214-9.*
Mazzoni et al. Dendritic Cell Modulation by Mast Cells Controls the Th1/Th2 Balance in Responsding T Cells. J. Immunol. 2006, 177:3577-3582.
Strik, et al. Human mast cells produce and release the cytotoxic lymphocyte associated protease granzyme B upon activation, Mol. Immunol. 2007, 44(14):3462-3672.
European Search Report dated Apr. 7, 2014 from European Patent Application No. 11825842.5, pp. 1-9.
Kaplan, Allen P. et al. Treatment of chronic autoimmune urticaria with omalizunab. Journal of Allergy and Clinical Immunology, Sep. 1, 2008, vol. 122, No. 8, pp. 569-573.
Fairley, J.A. et al. Pathogenicity of IgE in autoimmunity: Successful treatment of bullous pemphigoid with omalizunab. Journal of Allergy and Clinical Immunology, Mar. 1, 2009, vol. 123, No. 3, pp. 704-705.
Qu, Xiujuan et al. Selective Inhibition of FcRI-Medicated Mast Cell Activation by a Truncated Variant of Cbl-b Related to the Rat Model of Type 1 Diabetes Mellitus. Journal of Biochemistry, Jun. 1, 2005, vol. 137, No. 6, pp. 711-720.
Marone, G. et al. The Anti-IgE/Anti-FcepsilonRIalpha Autoantibody Network in Allergic and Autoimmune Diseases. Clinical and Experimental Allergy, Jan. 1, 1999, vol. 29, pp. 17-27.
Horn, Michael P. et al. Conditional autoimmunity mediated by human natural anti-FcepsilonRIalpha Autoantibodies? Conditional Autoimmune Reaction and Natural Autoantibodies, Oct. 1, 2001, vol. 15, No. 2, pp. 2268-2274.
Hashiguchi, Shuhei et al. Human FcvarepsilonRIalpha-Specific Human Single-Chain Fv (scFv) Antibody with Antagonistic Activity toward IgE/FcvarepsilonRIalpha-Binding. Journal of Biochemistry, Jan. 1, 2003, vol. 133, No. 1, pp. 43-49.
Rigby, L. J. et al. Monoclonal antibodies and synthetic peptides define the active site of Fc [epsilon] RI and a potential receptor antagonist. Allergy, Jul. 1, 2000, vol. 55, No. 7, pp. 609-619.
Fiegiber, Edda et al. Anti-FcepsilonRIalpha Autoantibodies in Autoimmune-mediated Disorders. J. Clin. Invest, Jan. 1, 1998, pp. 243-251.
Ying, Sun et al. TH1/TH2 cytokines and inflammatory cells in skin biopsy specimens from patients with chronic idiopathic urticaria: Comparison with the allergen-induced late-phase cutaneous reaction. J. Allergy Clin. Immunol., Apr. 2002, vol. 109, No. 4, pp. 694-700.
Lazarski, Christopher A. et al. IL-4 Attenuates Th1-Associated Chemokine Expression and Th1 Trafficking to Inflamed Tissues and Limits Pathogen Clearance. PLOS One, Aug. 2013, vol. 8, Issue 8, pp. 1-10.
Abdelilah, Soussi Gounni et al. Increased Expression of Th2-associated chemokines in bullous pemphigoid disease. Role of eosinophils in the production and release of these chemokines. Clinical Immunology, 2006(120): 220-231.

(Continued)

Primary Examiner — Michael Szperka
(74) Attorney, Agent, or Firm — MH2 Technology Law Group, LLP

(57) ABSTRACT

Methods of using anti-FceRI or anti-IgE antibodies for treating an autoimmune disease are disclosed. Also disclosed is a composition comprising an anti-FceRI antibody or anti-IgE antibody for use in treating an autoimmune disease. Also disclosed are non-antibody compounds that specifically activate basophils and/or mast cells, either by cross-linking IgE or FceRI, or by activating the cells through an FceRI-independent pathway and methods of using the same to treat autoimmune diseases.

12 Claims, 9 Drawing Sheets

(56) References Cited

OTHER PUBLICATIONS

Rizzo, C. et al. Direct characterization of human T cells in pemphigus vulgaris reveals elevated autoantigen-specific Th2 activity in association with active disease. Clinical and Experimental Dermatology, 2005(30): 535-540.

Aleksza, M. et al. Altered cytokine expression of peripheral blood lymphocytes in polymyositis and dermatomyositis. Ann. Rheum. Dis., 2005(64): 1485-1489.

Hase, Kayoko et al. Increased CCR4 expression in active systemic lupus erythematosus. Journal of Leukocyte Biology, Nov. 2001, vol. 70, pp. 749-755.

Poojary, K. Venuprasad et al. Control of Th2-Mediated Inflammation by Regulatory T Cells. AJP, Aug. 2010, vol. 177, pp. 525-531.

* cited by examiner

METHODS OF TREATING AUTOIMMUNE DISEASES WITH ANTI-FCεRI ANTIBODIES

CROSS REFERENCE TO RELATED APPLICATIONS

This application claims the benefit of, and relies on the filing date of, U.S. provisional patent application No. 61/382,541, filed 14 Sep. 2010, the entire disclosure of which is incorporated herein by reference.

STATEMENT OF GOVERNMENT INTEREST

The present invention arose in part from research funded by grants R073MX from the Uniformed Services University of the Health Sciences and 1DP2DK083131 from the National Institutes of Health. The U.S. Government may have certain rights in this invention.

BACKGROUND

The disease burden of the more than 80 distinct autoimmune diseases in the United States is enormous, collectively affecting 14 to 22 million people, an estimated 5-8% of the U.S. population.

Immunosuppression is the therapy of choice for most autoimmune diseases. Conventional agents that induce non-specific immunosuppression, such as non-steroidal anti-inflammatory drugs, glucocorticoids, and methotrexate have traditionally been the mainstay of therapy for many autoimmune diseases. While helpful, these medications are not always fully efficacious and are associated with significant toxicity when used chronically. Additionally, by non-specifically suppressing the immune system, these medications substantially increase patient susceptibility to infections.

Over the past few years, a number of new medications have become available which are able to specifically target certain arms of the immune response. While such approaches clearly represent a step forward in focusing immunosuppressive therapy, none does so in an antigen-specific manner. Consequently, these new medications still increase patient susceptibility to infections, albeit to a smaller range of organisms than non-specific immunosuppressive agents. This phenomenon is exemplified by the recent findings that tumor necrosis factor inhibitors, despite blocking the activity of only one cytokine, increase the risk of pneumonia, severe skin infections, and reactivation of prior tuberculosis.

Given the increased risk to infection that occurs when even specific facets of the immune system are inhibited, an alternative therapy for autoimmune diseases would be one that suppresses only self-reactive immune responses. Such a therapy would, ideally, be efficacious without compromising the body's ability to fight off infections. Several autoimmune diseases appear to be caused in large part by Th1-driven inflammation. Examples include type 1 diabetes, multiple sclerosis, Crohn's disease, inflammatory bowel disease, rheumatoid arthritis, and posterior uveitis. While the Th1/Th2 paradigm has evolved somewhat since its first description in 1986, it is still generally accepted that Th1 and Th2 responses have the ability to counter regulate each other. In particular, IL-4 suppresses differentiation of naïve T-cells into Th1 cells, resulting in decreased Th1 cytokine production and decreased Th1 cell proliferation in response to Th1-inducing antigens. Thus, there is a need for new treatment modalities that selectively down regulate Th1 responses.

SUMMARY

The present disclosure provides methods of treating an autoimmune disease by administering to a subject an antibody that binds to the Fc epsilon receptor I (FcεRI) or an IgE. Administering anti-FcεRI or anti-IgE antibodies activates basophils and mast cells. Without intending to be bound by any theory, we postulate that activated basophils and mast cells may protect against Th1-mediated autoimmune disease, for example, through the release of histamine or the synthesis of IL-4, both of which have been shown to counteract or suppress Th1-driven immune responses, or through the induction of negative feedback pathways that down regulate immune responses. The treatment methods described in this application may also be carried out using a non-antibody compound that specifically activates basophils and/or mast cells, either by cross-linking IgE or FcεRI, or by activating the cells through an FcεRI-independent pathway. These non-antibody compounds may also be formulated into compositions for use in therapy, as described herein.

One embodiment is directed to a method of treating a Th-1 mediated autoimmune disease in a subject, the method comprising administering to the subject an effective amount of an antibody, or antigen-binding fragment thereof, that binds to FcεRI or IgE, thereby treating the autoimmune disorder. In certain embodiments, the antibody is administered in an amount sufficient to crosslink the FcεRI on basophils and/or mast cells, thereby activating the basophils and/or mast cells. It is also possible to accomplish the treatment methods described herein using a compound, other than an antibody, that is capable of specifically activating basophils and mast cells, either by cross linking FcεRI or by crosslinking IgE antibodies bound to these receptors on basophils and/or mast cells, or by means of an FcεRI-independent pathway.

In one embodiment, the anti-FcεRI antibody or anti-IgE antibody is a monoclonal antibody. In another embodiment, the anti-FcεRI antibody or anti-IgE antibody is a chimeric antibody, a humanized antibody, or a human antibody. In one embodiment, the FcεRI is a human FcεRI. In yet another embodiment, the anti-FcεRI or anti-IgE antibody antibody is an IgG antibody or an IgE antibody. In one embodiment, the antigen binding site of the IgG antibody binds to the FcεRI. In another embodiment, the antigen binding site of the IgE antibody binds to an autoantigen.

In yet another embodiment, the Th1-mediated autoimmune disease is selected from type 1 insulin-dependent diabetes mellitus, scleroderma, multiple sclerosis, posterior uveitis, Crohn's disease, inflammatory bowel disease, and rheumatoid arthritis. In one embodiment, the subject is a mammal, preferably a human.

In another embodiment, the anti-FcεRI antibody or anti-IgE antibody is administered chronically to the subject. In one embodiment, the chronic administration comprises administering the anti-FcεRI antibody or anti-IgE antibody to the subject every week for at least 10 weeks. In another embodiment, the chronic administration comprises administering the anti-FcεRI antibody or anti-IgE antibody to the subject one or more times a day for at least 5, 7, 10, or 14 days.

Another aspect is directed to a composition comprising an anti-FcεRI antibody or anti-IgE antibody for use in therapy. In one embodiment the composition comprises an anti-FcεRI antibody or anti-IgE antibody for use in treating an autoimmune disease, including a Th1-mediated autoimmune disease, such as type 1 insulin-dependent diabetes mellitus, scleroderma, multiple sclerosis, posterior uveitis, Crohn's disease, inflammatory bowel disease, and rheumatoid arthritis. In one embodiment, the anti-FcεRI antibody or anti-IgE antibody is a monoclonal antibody. In another embodiment, the anti-FcεRI antibody or anti-IgE antibody is a chimeric antibody, a humanized antibody, or a human antibody. In yet another embodiment, the anti-FcεRI antibody or anti-IgE antibody is an IgG antibody or an IgE antibody. In one embodiment, the antigen binding site of the IgG antibody binds to the FcεRI. In another embodiment, the antigen binding site of the IgE antibody binds to an autoantigen. The composition optionally comprises a pharmaceutically acceptable excipient.

BRIEF DESCRIPTION OF THE DRAWINGS

The accompanying drawings, which are incorporated in and constitute a part of this specification, illustrate certain embodiments, and together with the written description, serve to explain certain principles of the antibodies and methods disclosed herein.

DETAILED DESCRIPTION

Figure 1A:
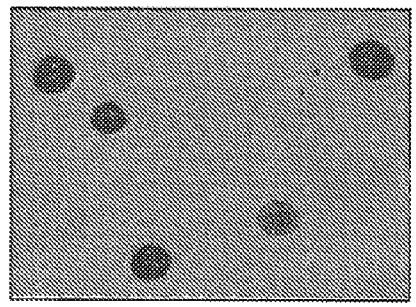
FIG. 1: Anti-FcεRI activates basophils and mast cells in vitro. (A) May-Grunwald staining of peritoneal mast cells after enrichment by density centrifugation. (B) Histamine release from mast cells in response to increasing concentrations of anti-FcER1. (C) Representative dot plots of intracellular IL-4 staining of basophils after incubation with media or anti-FcER1. Initial gating of lymphocytes and lower half of granulocyte region in FS/SS plot (left panel). Basophils identified as CD4−B220−IgE+ (middle panel). IL-4 staining of basophils after incubation with media (upper right panel) or anti-FcER1 (lower right panel). (D) Percentages of basophils that stain positively for IL-4 after incubation with media or anti-FcER1. (E) IL-4 release from whole blood after incubation with anti-FcER1. Error bars denote SEM. Statistical significance assessed per one-tailed paired T-test.

Reference will now be made in detail to various exemplary embodiments, examples of which are illustrated in the accompanying drawings. It is to be understood that the following detailed description is provided to give the reader a fuller understanding of certain embodiments, features, and details of aspects of the invention, and should not be interpreted as a limitation of the scope of the invention.

1. Definitions

In order that the present invention may be more readily understood, certain terms are first defined. Additional definitions are set forth throughout the detailed description.

The term "antibody" as used in this disclosure refers to an immunoglobulin or an antigen-binding fragment thereof. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda.

The terms "antigen-binding domain" and "antigen-binding fragment" refer to a part of an antibody molecule that comprises amino acids responsible for the specific binding between antibody and antigen. For certain antigens, the antigen-binding domain or antigen-binding fragment may only bind to a part of the antigen. The part of the antigen that is specifically recognized and bound by the antibody is referred to as the "epitope" or "antigenic determinant." Antigen-binding domains and antigen-binding fragments include Fab (Fragment antigen-binding); a $F(ab')_2$ fragment, a bivalent fragment having two Fab fragments linked by a disulfide bridge at the hinge region; Fv fragment; a single chain Fv fragment (scFv) see e.g., Bird et al. (1988) *Science* 242:423-426; and Huston et al. (1988) *Proc. Natl. Acad. Sci. USA* 85:5879-5883); a Fd fragment having the two $V_H$ and $C_H1$ domains; dAb (Ward et al., (1989) *Nature* 341:544-546), and other antibody fragments that retain antigen-binding function. The Fab fragment has $V_H$-$C_H1$ and $V_L$-$C_L$ domains covalently linked by a disulfide bond between the constant regions. The $F_v$ fragment is smaller and has $V_H$ and $V_L$ domains non-covalently linked. To overcome the tendency of non-covalently linked domains to dissociate, a $scF_v$ can be constructed. The $scF_v$ contains a flexible polypeptide that links (1) the C-terminus of $V_H$ to the N-terminus of $V_L$, or (2) the C-terminus of $V_L$ to the N-terminus of $V_H$. A 15-mer $(Gly_4Ser)_3$ peptide may be used as a linker, but other linkers are known in the art. These antibody fragments are obtained using conventional techniques known to those with skill in the art, and the fragments are evaluated for function in the same manner as are intact antibodies.

The term "effective amount" refers to a dosage or amount that is sufficient for treating an indicated disease or condition.

The term "human antibody" includes antibodies having variable and constant regions corresponding substantially to human germline immunoglobulin sequences known in the art, including, for example, those described by Kabat et al. (See Kabat, et al. (1991) Sequences of Proteins of Immunological Interest, Fifth Edition, U.S. Department of Health and Human Services, NIH Publication No. 91-3242), which is hereby incorporated by reference in its entirety. Human antibodies may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody can have at least one, two, three, four, five, or more positions replaced with an amino acid residue that is not encoded by the human germline immunoglobulin sequence.

The terms "treatment" or "treating" and the like refer to any treatment of any disease or condition in a mammal, e.g. particularly a human or a mouse, and includes inhibiting a disease, condition, or symptom of a disease or condition, e.g., arresting its development and/or delaying its onset or manifestation in the patient or relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans.

The term "pharmaceutically acceptable carrier" or "pharmaceutically acceptable excipient" means solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art.

The term "isolated," when used in the context of an antibody, refers to an antibody that is substantially free of its natural environment. For instance, an isolated protein is substantially free of cellular material or other proteins from the cell or tissue source from which it was derived. The term also refers to preparations where the isolated protein is sufficiently pure for pharmaceutical compositions; or at least 70-80% (w/w) pure; or at least 80-90% (w/w) pure; or at least 90-95% pure; or at least 95%, 96%, 97%, 98%, 99%, or 100% (w/w) pure.

As understood in the art, the term "Th1-mediated autoimmune disease" means an autoimmune disease that is associated with a type 1 helper T cell (Th1) response. Such diseases include, but are not limited to, type 1 insulin-dependent diabetes mellitus, scleroderma, multiple sclerosis, posterior uveitis, Crohn's disease, inflammatory bowel disease, and rheumatoid arthritis.

The term "chronically administered" or the like means that the antibody or other molecule is administered to the subject at least as frequently as once a week for at least 10 weeks or at least as frequently as one or more times a day for at least 5 days.

The term "amount sufficient to crosslink the FcεRI" refers to an amount of a compound, such as an anti-FcεRI antibody or anti-IgE antibody, that is sufficient to crosslink and aggregate the FcεRI on basophils and/or mast cells, such that the basophils and/or mast cells are stimulated to release IL-4 or histamine. Release of IL-4 or histamine can be measured using techniques known in the art, including those disclosed in this application.

2. Th1/Th2 Immune Responses

CD4 T helper cell responses to antigens can be classified based on the cytokines they produce. Type 1 helper T cells (Th1) produce inflammatory cytokines, such as IFN-γ, IL-2, TNF-α, and TNF-β. Th1 cells activate macrophages and are associated with cell-mediated immune responses. Type 2 helper cells (Th2), on the other hand, typically produce cytokines, such as IL-4, IL-5, IL-10, and IL-13. Th2 cells activate B cells and are associated with antibody-mediated immune responses.

3. Autoimmune Diseases

Autoimmune diseases are characterized by overactive, immune responses to self antigens expressed on cells. In essence, the immune system mistakes a self antigen in the body as a pathogen and mounts an attack against the cell or tissue expressing the self antigen. Autoimmune diseases usually involve chronic autoimmune responses, leading to long-term tissue damage. Several autoimmune diseases appear to be caused in large part by Th1-driven inflammation based, in part, on cytokine profiles, including predominantly high levels of IFN-γ. Examples of Th1-mediated autoimmune diseases, include, but are not limited to, type-1 insulin-dependent diabetes mellitus, multiple sclerosis, Crohn's disease, inflammatory bowel disease, rheumatoid arthritis, and posterior uveitis.

4. Anti-FcεRI Therapy for Autoimmune Diseases

The prevalence of Type 1 diabetes and other autoimmune diseases has increased sharply over the past few decades (1-6). While genetic factors play a role in susceptibility to Type 1 diabetes, the dramatic worldwide increase in the prevalence of Type 1 diabetes is probably due to changes in environmental factors.

One environmental change that may play a part in the recent increase in autoimmune diseases is the loss of chronic parasitic worm infections in developed countries. Multiple studies have found that individuals infected with chronic parasitic worm infections have lower rates of autoimmune diseases than others living in the same environment (reviewed in (7)). Experimentally, parasitic worms have been shown to protect against Type 1 diabetes and other autoimmune diseases in several animal models (8-10), and in humans, oral administration of porcine whipworm eggs results in protection against inflammatory bowel disease (11).

Until recently, most people had lifelong infections with parasitic worms. As helminths have been identified in neolithic and pre-Columbian mummies (12, 13), it is likely that the human immune system evolved in the setting of chronic infection with these parasites (14). Consequently, it has been posited that the loss of parasitic worm infections is partially responsible for the increased prevalence of autoimmune and allergic diseases in developed countries—the notion being that now, in the absence of the immunomodulatory responses triggered by helminths, our immune systems have become hyperresponsive (9, 14, 15).

Unlike most bacterial or viral pathogens, helminth infections induce the production of specific IgE. This IgE binds to basophils and mast cells through the Fc epsilon receptor I (FcεRI), the high affinity IgE receptor (51). Helminth specific antigens can then activate basophils and mast cells by crosslinking IgE molecules and aggregating FcεRIs. As helminths are large organisms that release substantial amounts of antigen, and as these infections last for years, helminth infections likely induce a state of chronic basophil and mast cell activation. Indeed, recent time course studies in our lab demonstrate that both chronic basophil activation (18) and chronic mast cell activation (E. Mueller, E. Mitre, unpublished data) occur during infection of mice with the filarial nematode *Litomosoides sigmodontis*.

Without intending to be bound by any theory, there are at least two likely mechanistic rationales for postulating that chronic activation of basophils and mast cells may protect against Th1-driven autoimmune disease. First, factors released by basophils and mast cells may have direct immunomodulatory properties that are protective against Th1-mediated autoimmune diseases. Basophils, for example, release large quantities of IL-4 when activated and have been shown to do so in response to parasite antigen in filaria-infected patients (17) as well as in animal models of helminth infection (18-21). As destruction of β-islet cells in Type 1 diabetes is driven by IFN-γ release from Th1 cells, and as IL-4 counter regulates Th1 responses and has been shown to improve Th1-driven autoimmune diseases (22, 23), chronic basophil activation may protect against Type 1 diabetes by release of IL-4. Similarly, histamine, which is released from both basophils and mast cells, has been shown in vitro to suppress Th1 responses by signaling through the H2 receptor on lymphocytes (24). Alternatively, chronic activation of basophils and mast cells could induce negative feedback pathways that tamp down ongoing autoimmune responses. Interestingly, there is substantial evidence that chronic immunotherapy, in which patients with IgE-mediated allergies are given weekly injections of allergen, augments immune regulatory networks such as the suppressive cytokine IL-10 and natural T-regulatory cells (25, 26).

To determine whether recapitulation of the IgE-mediated immune responses induced by helminths can afford protection against autoimmunity in the absence of actual infection, basophils and mast cells were activated in non-obese diabetic (NOD) mice using an anti-FcεRI antibody. NOD mice spontaneously develop Type 1 diabetes (also known as insulin dependent diabetes mellitus), a form of diabetes that develops from the autoimmune destruction of the insulin-producing beta islet cells of the pancreas. NOD mice are an art recognized animal model for Type 1 diabetes (50).

To activate basophils and mast cells in vivo, NOD mice were treated with weekly or daily injections of anti-FcεRI antibody. In vitro experiments demonstrated that anti-FcεRI activates both basophils and mast cells. Intraperitoneal injections of anti-FcεRI resulted in release of large amounts of IL-4 and histamine into the bloodstream, consistent with in vivo basophil and mast cell activation, and resulted in a Th2 shift in insulin-specific antibody production. While production of IL-10 and frequencies of splenic and pancreatic lymph node CD4+CD25+FoxP3+ regulatory T cells were not significantly altered, both of these parameters trended higher in anti-FcεRI-treated animals. Consistent with our hypothesis, anti-FcεRI-treated NOD mice exhibited significant delays in the onset of autoimmune diabetes and substantially improved survival rates of NOD mice. IL-4 responses appear to play a partial role underlying this phenomenon as the protective effect afforded by anti-FcεRI therapy was diminished in IL-4 deficient NOD mice. In contrast, signaling of histamine through H1 and H2 receptors did not appear to play a role, as anti-FcεRI-mediated protection was not reduced in mice treated with H1 and H2 receptor blockers.

These results demonstrate that anti-FcεRI therapy can delay the onset of Type I diabetes in NOD mice and suggest that chronic activation of basophils and mast cells represent a new avenue of therapy for Th1-associated autoimmune diseases.

5. Fc Epsilon Receptor I

As discussed above, FcεRI is a receptor complex expressed on mast and basophil cells. The tetrameric FcεRI complex comprises an FcεRIα subunit combined with one β and two γ subunits. The FcεRI complex binds to the Fc portion of IgE antibodies and, thus, plays an important role in triggering IgE-mediated allergic reactions. The binding of anti-FcεRI antibodies to FcεRI on the surface of mast cells and/or basophils leads to the crosslinking of FcεRI. Crosslinking of FcεRI in turn results in the degranulation of the mast cells and/or basophils, stimulating the release of vasoactive amines, such as histamine, and, thus, mimics the effect of crosslinked IgE bound to FcεRI. Activated mast cells and basophils also synthesize and secrete cytokines, such as IL-4, that contribute to the local inflammatory reaction. As noted above, IL-4 is a cytokine associated with Th2 cells and has been shown to improve Th1-driven autoimmune diseases (22, 23).

6. Anti-FcεRI Antibodies

This disclosure provides antibodies that bind to FcεRI or antibodies that bind to IgE for use in treating autoimmune diseases, such as Type 1 diabetes. The antibodies provided in this disclosure that bind to FcεRI are optionally isolated. In a preferred embodiment, the antibodies bind to human FcεRI. The anti-FcεRI antibodies can bind to the FcεRI complex or a subunit thereof (FcεRIα, FcεRI, or FcεRIγ).

Antibodies, also known as immunoglobulins, are typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain includes an N-terminal variable (V) domain (VL) and a constant (C) domain (CL). Each heavy chain includes an N-terminal V domain (VH), three or four C domains (CHs), and a hinge region. The CH domain most proximal to VH is designated as CH1. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. Identification and numbering of framework and CDR residues is as described by Chothia et al., Structural determinants in the sequences of immunoglobulin variable domain, J Mol Biol 1998, 278:457-79, which is hereby incorporated by reference in its entirety.

CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see *Antibodies: A Laboratory Manual, Cold Spring Harbor Laboratory*, eds. Harlow et al., 1988. One skilled in the art will recognize that each subunit structure, e.g., a CH, VH, CL, VL, CDR, FR structure, comprises active fragments, e.g., the portion of the VH, VL, or CDR subunit the binds to the antigen, i.e., the antigen-binding fragment, or, e.g., the portion of the CH subunit that binds to and/or activates, e.g., an Fc receptor and/or complement. The CDRs typically refer to the Kabat CDRs, as described in *Sequences of Proteins of Immunological Interest, US Department of Health and Human Services* (1991), eds. Kabat et al. Another standard for characterizing the antigen binding site is to refer to the hypervariable loops as described by Chothia. See, e.g., Chothia, D. et al. (1992) *J. Mol. Biol.* 227:799-817; and Tomlinson et al. (1995) *EMBO J.* 14:4628-4638. Still another standard is the AbM definition used by Oxford Molecular's AbM antibody modelling software. See, generally, e.g., *Protein Sequence and Structure Analysis of Antibody Variable Domains. In: Antibody Engineering Lab Manual* (Ed.: Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops.

An antibody fusion protein may be prepared that has dual Fc regions with both enhanced complement lysis and ADCC capabilities. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, *Annu. Rev. Immunol* 9:457-92, 1991; Capel et al., *Immunomethods* 4:25-34, 1994; and de Haas et al., *J. Lab. Clin. Med.* 126:330-41, 1995).

7. Methods of Making Antibodies

Methods of making antibodies, or antigen-binding fragments thereof, and formulating the same for therapeutic administration are well known as discussed, for example, in PCT/US2010/032714, which is hereby incorporated by reference in its entirety.

For example, antibodies can be produced using recombinant DNA methods. See, e.g., U.S. Pat. No. 4,816,567, EPO 8430268.0; EPO 85102665.8; EPO 85305604.2; PCT/GB85/00392; EPO 85115311.4; PCT/US86/002269; and Japanese application 85239543, the disclosures of which are incorporated herein by reference in their entirety.

Monoclonal antibodies may also be produced by preparing immortalized cell lines capable of producing antibodies having desired specificity. Such immortalized cell lines may be produced in a variety of ways. Conveniently, a small vertebrate, such as a mouse, is hyperimmunized with the desired immunogen. The vertebrate is then sacrificed, usually several days after the final immunization, the spleen cells removed, and the spleen cells immortalized. The most common technique is fusion with a myeloma cell fusion partner, as first described by Kohler and Milstein (1975) Nature 256:495-497. Other techniques including EBV transformation, transformation with bare DNA, e.g., oncogenes, retroviruses, etc., or any other method which provides for stable maintenance of the cell line and production of monoclonal antibodies. Specific techniques for preparing monoclonal antibodies are described in Antibodies: A Laboratory Manual, Harlow and Lane, eds., Cold Spring Harbor Laboratory, 1988, the full disclosure of which is incorporated herein by reference.

Immortalized cell lines can be screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

One exemplary method of making antibodies includes screening protein expression libraries, e.g., phage or ribosome display libraries. Phage display is described, for example, in Ladner et al., U.S. Pat. No. 5,223,409; Smith (1985) *Science* 228:1315-1317; Clackson et al. (1991) *Nature*, 352: 624-628; Marks et al. (1991) *J. Mol. Biol.*, 222: 581-597 WO 92/18619; WO 91/17271; WO 92/20791; WO 92/15679; WO 93/01288; WO 92/01047; WO 92/09690; and WO 90/02809, the disclosures of which are incorporated herein by reference in their entirety.

In addition to the use of display libraries, the specified antigen (e.g. FcεRI or a subunit thereof) can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) *Nature Genetics* 7:13-21, US 2003-0070185, WO 96/34096, published Oct. 31, 1996, and PCT Application No. PCT/US96/05928, filed Apr. 29, 1996, the disclosures of which are incorporated herein by reference in their entirety.

In another embodiment, a monoclonal antibody is obtained from the non-human animal, and then modified. For example, humanized, deimmunized, and chimeric antibodies may be produced using recombinant DNA techniques known in the art. A variety of approaches for making chimeric antibodies have been described. See e.g., Morrison et al., *Proc. Natl. Acad. Sci. U.S.A.* 81:6851, 1985; Takeda et al., *Nature* 314: 452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B, the disclosures of which are incorporated herein by reference in their entirety. Humanizing an antibody involves transplanting the combining-site of a nonhuman antibody onto a human antibody. This may be performed by grafting the nonhuman CDRs onto human framework and optionally human constant regions or by transplanting the entire nonhuman variable domains but hiding them with a human-like surface by replacement of certain exposed residues. Details on creating a humanized antibody are disclosed in U.S. Pat. No. 5,472,693, which is hereby incorporated by reference.

Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539, the disclosure of which is incorporated herein by reference in its entirety). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) *Science* 229:1202-1207; by Oi et al. (1986) *BioTechniques* 4:214; and by U.S. Pat. No. 5,585,089; U.S. Pat. No. 5,693,761; U.S. Pat. No. 5,693,762; U.S. Pat. No. 5,859,205; and U.S. Pat. No. 6,407,213, the disclosures of which are incorporated herein by reference in their entirety. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., *Proc. Natl. Acad. Sci. U.S.A.*, 80: 7308-7312, 1983; Kozbor et al., *Immunology Today*, 4: 7279, 1983; Olson et al., *Meth. Enzymol.*, 92: 3-16, 1982), the disclosures of which are incorporated herein by reference in their entirety, and may be made according to the teachings of PCT Publication WO92/06193 or EP 0239400, the disclosures of which are incorporated herein by reference in their entirety. Typically, conservative substitutions are made. Often, but not exclusively, an amino acid common to a position in human germline antibody sequences may be used. Human germline sequences, e.g., are disclosed in Tomlinson, et al. (1992) *J. Mol. Biol.* 227:776-798; Cook, G. P. et al. (1995) *Immunol. Today* Vol. 16 (5): 237-242; Chothia, D. et al. (1992) *J. Mol. Biol.* 227:799-817; and Tomlinson et al. (1995) *EMBO J.* 14:4628-4638, the disclosures of which are incorporated herein by reference in their entirety. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064, the disclosure of which is incorporated herein by reference in its entirety.

Human antibodies can be generated using methods known in the art, such as phage display technology. Phage display technology mimics the mammalian immune system by cloning large libraries of antibody genes and selecting for binding to a desired target, such as the FcεRI or a subunit thereof. The libraries used in phage display technology can be made from several sources. For example, an immune library, created from humans exposed to a desired antigen through vaccination or disease, has high levels of circulating antibodies to the antigen even when the library is relatively small. As another example, a naïve library, made from mRNA isolated from non-immunized individuals, can be used repeatedly to isolate antibodies against a variety of antigens. As still another example, a synthetic library, in which germline antibody gene segments are cloned and arranged combinatorially in vitro to reconstitute genes encoding complete $V_H$ and $V_L$ chains, has the advantage of producing antibodies with specificity to self-antigens. Semi-synthetic libraries can also be made by selecting one or more antibody frameworks and randomizing sequences within the CDR loops.

In phage display technology, once a library is created, it is fused to a surface protein of phages, commonly pIII. In a process known as panning, phages displaying an antibody specific for the antigen of interest are enriched by selective adsorption onto immobilized antigen. Subsequently, the bound phage can be eluted from the surface and amplified through infection of *E. coli* cells.

Other modifications of phage display technology to generate human antibodies are also known in the art. For example, antibodies can be displayed on the surfaces of microbial cells, such as *E. coli* and *Saccharomyces cerevisaie*, instead of on the surface of bacteriophages. In this case, screening can be performed by incubation with a fluorescently tagged ligand in buffer. Cells that display the antibodies that bind to the ligand become fluorescently labeled and are isolated by fluorescence-activated cell sorting. Another modification, termed ribosome display, relies on the formation of a ternary complex between ribosomes, mRNA, and the polypeptide.

Another method known in the art to produce human antibodies is one that uses transgenic mice. The native immunoglobulin repertoire in these mice has been replaced with human V-genes in the murine chromosome. The mice can be injected with a desired antigen and the resulting antibodies can be recovered by cloning and screening an immune library, or by conventional hybridoma technology. These mice produce significant levels of fully human antibodies that only differ in glycosylation patterns.

8. Methods of Use

The antibodies described herein that bind to FcεRI can be used in a variety of research and medical applications. In one aspect, the disclosure provides a method of treating an autoimmune disease in a subject, comprising administering to said subject an effective amount of an antibody that binds to FcεRI formulated in a pharmaceutically acceptable vehicle. Preferably, the autoimmune disease is a Th1-mediated autoimmune disease, including, but not limited to type-1 insulin-dependent diabetes mellitus, multiple sclerosis, Crohn's disease, inflammatory bowel disease, rheumatoid arthritis, and posterior uveitis.

9. Formulations and Administration

The disclosure provides compositions comprising an antibody that binds to FcεRI. In certain embodiments, the compositions are suitable for pharmaceutical use and administration to patients. These compositions comprise an antibody that binds to FcεRI and a pharmaceutically acceptable excipient. The compositions may also contain other active compounds providing supplemental, additional, or enhanced therapeutic functions. The pharmaceutical compositions may also be included in a container, pack, or dispenser together with instructions for administration. In one embodiment, the composition comprises a monoclonal antibody that binds to FcεRI for use in treating an autoimmune disease, including a Th1-mediated autoimmune disease, such as type-1 insulin-dependent diabetes mellitus, multiple sclerosis, Crohn's disease, inflammatory bowel disease, rheumatoid arthritis, and posterior uveitis.

A pharmaceutical composition of the invention is formulated to be compatible with its intended route of administration. Methods to accomplish the administration are known to those of ordinary skill in the art. This includes, for example, injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically contemplated, by such means as depot injections or erodible implants. Localized delivery is particularly contemplated, by such means as delivery via a catheter to one or more arteries, such as the renal artery or a vessel supplying a localized tumor.

In one embodiment a subject antibody is administered to a patient by injection (e.g., intraperitoneally, intravenously, subcutaneously, intramuscularly, etc.). The antibody may be administered, for example, by bolus injunction or by slow infusion. Slow infusion over a period of 30 minutes to 2 hours may be used. Generally, for administration of anti-FcεRI antibodies, an initial candidate dosage can be about 5-100 µg/kg (0.005-0.1 mg/kg). A typical daily dosage might range from about any of 0.001 mg/kg to about 100 mg/kg; about 0.01 mg/kg to about 10 mg/kg; or about 0.1 mg/kg to about 5 mg/kg. The appropriate dosage of the anti-FcεRI antibody will depend on various factors, including the antibody used (or compositions thereof), route of administration, frequency of administration, patient's health, age, or size, the type and severity of the disease to be treated, whether the agent is administered for preventive or therapeutic purposes, previous therapy, the patient's clinical history and response to the antibody, and the discretion of the attending physician. Typically, the clinician will administer an anti-FcεRI antibody until a dosage is reached that achieves the desired result.

For repeated administrations over several days or longer, depending on the condition, the treatment is sustained until a desired suppression of symptoms occurs or until sufficient therapeutic levels of the antibody are achieved. An exemplary dosage regimen comprises administering a daily dose of about 5-100 µg/kg for about 5-14 days (or longer), with or without weekly maintenance doses of about 100-250 µg/kg. Alternatively, an exemplary dosing regimen comprises administering an initial dose of about 5-100 µg/kg, followed by a weekly maintenance dose of about 5-250 µg/kg of the anti-FcεRI antibody, or followed by a maintenance dose of about 5-250 µg/kg every other week. However, other dosage regimens may be useful, depending on the pharmacokinetic parameters that the practitioner wishes to achieve. For example, dosing from one to four times a week is contemplated. In some embodiments, dosing frequency is once every day, every other day, every third day, every fourth day, every fifth day, every sixth day; once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays.

The dosing regimen can also vary over time. One risk of anti-FcεRI therapy is the induction of anaphylaxis, resulting from chronic mast cell and basophil activation. To reduce this risk, it is possible to initiate treatment with smaller doses of anti-FcεRI antibodies followed by a gradual increase in treatment dosage. Such an approach would be similar to allergen immunotherapy, where the allergen dose is gradually increased over time. Allergen immunotherapy induces repeated basophil and mast cell activation and is routinely conducted in the outpatient arena for diseases as benign as allergic rhinitis. Thus, in one embodiment, the anti-FcεRI therapy can be administered at a smaller initial dose followed by gradually increasing doses. The particular dosage regimen, i.e., dose, timing and repetition, will depend on the particular individual and that individual's medical history, as well as the properties of the anti-FcεRI antibody (such as the half-life of the antibody and other considerations well known in the art).

Toxicity and therapeutic efficacy of the composition can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antibodies that exhibit large therapeutic indices may be less toxic and/or more therapeutically effective.

EXAMPLES

To test whether chronic activation of basophils and mast cells can protect against a Th1-driven autoimmune disease, the effects of repeated anti-FcεRI antibody injections on the development of Type 1 diabetes in the NOD mouse model were studied. The studies demonstrate that anti-FcεRI therapy activates basophils and mast cells, induces IL-4 and histamine release in vivo, and delays Type 1 diabetes onset and enhances survival in the NOD mouse. Studies using IL-4-deficient NOD mice and therapeutic histamine blockade reveal that IL-4, but not histamine signaling through H1 or H2 receptors, plays a partial role in the protective effects of anti-FcεRI therapy.

Material & Methods

Mice:

Female NOD and IL-4-deficient NOD.129P2(B6)-Ile$^{tm1Cgn}$/DvsJ mice (The Jackson Laboratory, Bar Harbor, Me.) were maintained at the Uniformed Services University (USU) animal facility with free access to food and water. All experiments were performed under protocols approved by the USU Institutional Animal Care and Use Committee.

Assessment of Diabetes:

Glucose levels of mice were determined from blood taken by orbital bleeds every other week using a standard blood glucose meter (Accu-Check® Advantage, Roche Diagnostics GmbH). Mice with glucose levels greater than 230 mg/dl in two consecutive measurements were considered diabetic.

Treatment with Anti-FcεRI Antibody:

Beginning at 6 weeks of age, mice were given weekly i.p. injections of 50 µg Armenian hamster anti-mouse FcεRI (MAR-I, eBioscience, San Diego, Calif.) or control Armenian hamster IgG (Isotype Control, Functional Grade Purified, eBioscience, San Diego, Calif.) throughout the experiment. Subsets of animals were euthanized at 16 weeks of age, one day after the last anti-FcεRI or IgG injection, to assess pancreas inflammation, splenic and pancreatic lymph node cytokine production, cell subtypes, as well as insulin-specific IgG1 and IgG2c levels. Different shorter anti-FcεRI treatment regiments were tested starting at 6-weeks of age. Those regimens included weekly i.p. injections of 50 µg anti-FcεRI or control IgG for four weeks and i.p. injections of 25 and 50 µg anti-FcεRI or control IgG twice a week for four weeks. In a separate experiment, beginning at 12 weeks of age, mice were given i.p. injections of 5 µg Armenian hamster anti-mouse FcεRI (MAR-I, eBioscience, San Diego, Calif.) or control Armenian hamster IgG (Isotype Control, Functional Grade Purified, eBioscience, San Diego, Calif.) daily for 10 consecutive days.

Assessment of Pancreas Inflammation:

At 16 weeks of age, pancreases were isolated and fixed in 10% formalin. Haematoxylin-eosin stained slices were assessed for inflammation by a pathologist blinded to the intervention group. Total numbers of islets of three longitudinal sections 400 µm apart of each pancreas were assessed. The severity of insulitis was scored as non-infiltrated, periinsulitis (lymphocytes at the periphery of islets), or intrainsulitis (lymphocyte infiltration into the interior of the islets lesser or greater than 50%).

Spleen and Pancreatic Lymph Node Cell Culture:

At 16 weeks of age, animals that were treated for 10 weeks with either anti-FcεRI or control IgG were euthanized and spleen and pancreatic lymph nodes were isolated. Spleen and pancreatic lymph node cells were prepared and cultured as previously reported (8). In brief, single cell suspensions were obtained, red blood lysis performed for spleen cells (ACK Lysing Buffer, Quality Biological, Inc., Gaithersburg, Md.), and cells were plated at a concentration of $2\times10^6$ cells/ml in enriched media (Iscove's Dulbecco modified medium (Mediatech, Manassas, Va.) including 10% fetal calf serum (Valley Biomedical, Winchester, Va.), 1% L-glutamine (Mediatech, Gaithersburg, Md.), 1% insulin-transferrin-selenium medium (Invitrogen Inc., Carlsbad, Calif.) and 80 µg/ml gentamicin (Quality Biological, Inc., Gaithersburg, Md.)), stimulated with 5 µg/ml anti-CD3 and 2 µg/ml anti-CD28 (eBioscience, San Diego, Calif.), and cultured at 37° C., 5% $CO_2$.

Flow Cytometric Analysis of Regulatory T Cells and Intracellular Cytokine Production by T Cells:

Spleen and pancreatic lymph node cells were cultured as described above and prepared for flow analysis as previously reported (8). In brief, after two hours of incubation, BD GolgiStop™ was added (BD Biosciences, Franklin Lake, N.J.) and cells were incubated for an additional four hours. Collected cells were fixed and permeabilized (eBioscience, San Diego, Calif.) overnight. For analysis cells were washed once with phosphate-buffered saline (PBS)/1% BSA (bovine serum albumin, Sigma, St. Louis, Mo.), followed by a blocking step with PBS/1% BSA. Cells were washed with 1× permeabilization buffer (eBioscience, San Diego, Calif.) and stained for five- or four-color-flow using CD4 PerCP, IL-4 APC (BD Biosciences, Franklin Lake, N.J.), CD8a Pacific Blue, gamma interferon (IFN-γ) FITC, and IL-17 PE (eBioscience, San Diego, Calif.) or CD4 PerCP (BD Biosciences, Franklin Lake, N.J.), FoxP3 FITC, CD25 APC-Alexa Fluor 750, and IL-10 PE (eBioscience, San Diego, Calif.). For identification of regulatory CD8 T-cells and regulatory B cells, fixed, cryopreserved (PBS/10% DMSO) spleen cells were washed once, blocked with CD16/CD32 (BD Biosciences, Franklin Lake, N.J.) and stained with CD4 Qdot 605 (Invitrogen, Carlsbad, Calif.), CD8 PE Cy5, FoxP3 FITC, (eBioscience, San Diego, Calif.) or B220 PerCP, CD1d FITC, CD5 APC (all BD Bioscience), and IL-10 PE (eBioscience, San Diego, Calif.). Flow cytometry was performed using a BD LSR11 system and subsequently analyzed with FACS-DiVa 6.1 software (BD Biosciences, Franklin Lake, N.J.).

Measurement of Cytokines and Antibodies by ELISA:

Cytokine enzyme-linked immunosorbent assays (ELISAs) were performed from spleen and pancreatic lymph node cell cultures. Culture supernatants from cells that were cultured as described above and stimulated with anti-CD3 and anti-CD28 were collected after 72 h of incubation. IFN-γ, IL-4, IL-5, and IL-10 were quantified according to the manufacturer's instructions (BD Biosciences, Franklin Lake, N.J.).

Plasma derived insulin-specific IgG1 and IgG2c were analyzed by sandwich ELISA as previously described (8). All samples were analyzed as duplicates at the same time on the same plate to allow accurate comparison between groups by OD.

Flow Cytometric Analysis of Basophils and Mast Cells:

Frequency of basophils in the peripheral blood and peritoneal mast cells was measured by flow cytometry one day after a single injection of 50 µg anti-FcεRI or control IgG in 8-week old female NOD mice.

Basophil flow was performed as previously described (16). In brief, 100 µl of blood obtained by orbital bleeding was diluted with 100 µl of RPMI media (RPMI-1640, Mediatech, Manassas, Va.), red blood cells lysed and cells fixed (whole blood lysing reagent kit, Beckman Coulter, Inc., Indianapolis, Ind.). After two washing steps with 1×PBS, cells were blocked overnight with PBS/1% BSA. Cells were washed and stained with IgE FITC (BD Biosciences, Franklin Lake, N.J.), CD4 PerCP (BD Biosciences, Franklin Lake, N.J.) and B220 PerCP (BD Biosciences, Franklin Lake, N.J.). During flow cytometric analysis, basophils were identified as CD4–/B220–/IgE+ cells.

Mast cells were obtained by a peritoneal wash with 1×HBSS (Gibco, Carslbad, Calif.) and fixed after red blood cell lysis (whole blood lysing reagent kit, Beckman Coulter Inc., Indianapolis, Ind.). Cells were washed once and blocked overnight in PBS/1% BSA. $1\times10^6$ peritoneal cells were stained for flow with IgE FITC (BD Biosciences, Franklin Lake, N.J.) and cKit APC (BD Biosciences, Franklin Lake, N.J.). During flow cytometric analysis, mast cells were identified as IgE+/cKit+ cells.

Detection of Histamine from In Vitro Stimulated Purified Mast Cells:

For in vitro activation of mast cells, peritoneal mast cells were purified using a 70% percoll gradient. 2000 mast cells were cultured in 250 µl histamine release buffer (Immunotech S.A.S., Marseille, France) and stimulated with isotype (10 µg/ml) or anti-FcεRI (0.4, 1.6, 6.25, 25, 100 µg/ml) for 30 minutes. Cells were acylated and the histamine ELISA was performed according to the manufacturer's instructions (Immunotech S.A.S., Marseille, France).

Intracellular IL-4 Detection of In Vitro Stimulated Basophils:

For intracellular IL-4 detection of basophils, 100 μl of peripheral blood from NOD mice was cultured with GolgiStop (BD Bioscience, Franklin Lake, N.J.) and either media, 10 μg/ml isotype control, 10 or 25 μg/ml anti-FcεRI (MAR-1) for a total of 6 h at 37° C. Following red blood lysis and fixation (performed as mentioned above) cells were stained in a two step procedure for flow. Cells were stained for the surface markers IgE FITC, CD4 PerCP, and B220, followed by permeabilization (permeabilization buffer, BD Bioscience, Franklin Lake, N.J.) and staining with IL-4 APC (BD Bioscience, Franklin Lake N.J.).

As basophils are the only circulating cells in mice that express FcεRI, IL-4 release from whole blood was measured after in vitro stimulation of 100 μl of peripheral blood from NOD mice cultured with 10 μg/ml anti-FcεRI antibody, 10 μg/ml IgG isotype control, or media for 6 h at 37° C. Plasma was obtained by centrifugation and stored at −20° C. until the IL-4 ELISA was performed as per the manufacturer's instructions (eBioscience, San Diego, Calif.).

In Vivo Cytokine Capture Assay to Detect IL-4 Release after Anti-FcεRI Injection:

10 μg biotinylated IL-4 antibody (BD Bioscience, Franklin Lake, N.J.) was injected i.p. into 11-week old NOD mice. The following day mice were injected i.p. with 50 μg anti-FcεRI or control IgG and one day later blood was collected by orbital bleed. Concentration of IL-4 was measured by ELISA according to the manufacturer's instructions (BD Biosciences, Franklin Lake, N.J.).

Detection of In Vivo Histamine Release after Injection of Anti-FcεRI:

Mice were i.p. injected with a single dose of 50 μg anti-FcεRI or control IgG. After 30 minutes, blood was collected by orbital bleed. 100 μl of blood were immediately acylated and histamine ELISA was performed according to the manufacturer's instructions (Immunotech S.A.S., Marseille, France).

Treatment with Histamine Receptor Blockers:

Starting at 6-weeks of age, 2.5 mg/ml cimetidine (Sigma, St. Louis, Mo.), an $H_2$-receptor blocker, and 0.25 mg/ml fexofenidine HCl (TEVA Pharmaceuticals, Washington, D.C.), an $H_1$-receptor blocker, were added to the drinking water of NOD mice. The treated drinking water was freshly prepared every other day throughout the experiment until 25 weeks of age.

Efficacy of $H_2$-receptor blockage was tested by measuring the stomach pH, 2 days after changing the drinking water in mice that had been receiving fexofenidine and cimetidine treatments for 2 weeks. Mice were euthanized and the stomach pH was measured using pH strips (Micro Essential Laboratory, Brooklyn, N.Y.). In addition, blockage of the histamine-receptors was confirmed in vivo by injecting 10 μg anti-FcεRI intradermally into one ear and 10 μg control IgG in the other, followed by i.v. injection of 200 μl toluidine blue (Sigma, St. Louis, Mo., 0.5% in PBS) 3 minutes later. The ears were dissected 10 min later and vascular permeablility was measured at 620 nm by the optical density (OD) of the blue dye extracted from the ears after o.n. incubation at 63° C. in formamide (Sigma, St. Louis, Mo.).

Statistics:

Statistical analyses were performed with GraphPad Prism software (GraphPad Software). Differences between paired groups for in vitro studies were analyzed using one-tailed paired T-test and differences between two unpaired groups for in vivo studies were tested for significance with the Mann-Whitney-U-test. P-values <0.05 were considered significant. All experiments were performed at least twice.

Example 1

Anti-FcεRI Antibody Activates Basophils and Mast Cells of NOD Mice

Figure 1B:
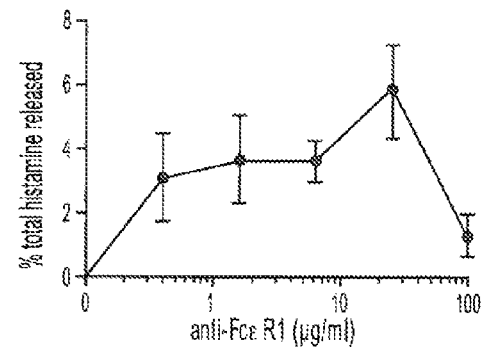

To evaluate the effects of anti-FcεRI antibody on mast cells in vitro, histamine release from mast cells purified from the peritoneal cavity of NOD mice was assessed in response to in vitro incubation with various concentrations of anti-FcεRI. Density gradient centrifugation of peritoneal cells resulted in high level enrichment of mast cells (>70% purity for all samples, FIG. 1A). While incubation of enriched mast cells with media or isotype antibody resulted in no demonstrable histamine release above incubation with media alone, incubation with increasing concentrations of anti-FcεRI antibody resulted in a classical mast cell activation curve (FIG. 1B).

Figure 1C:
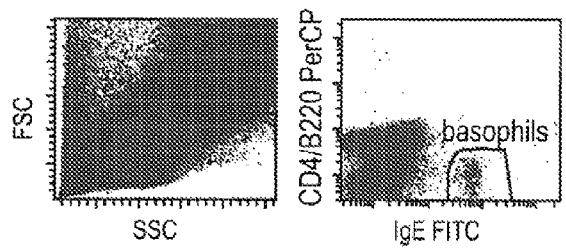
Figure 1D:
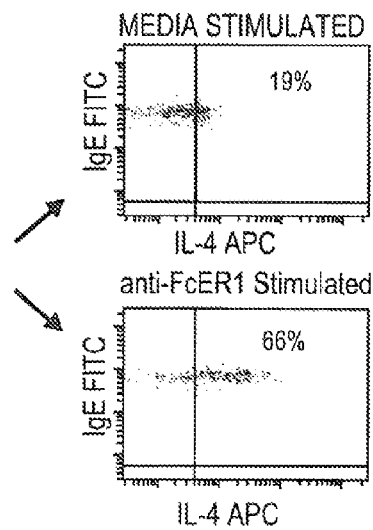
Figure 1D:
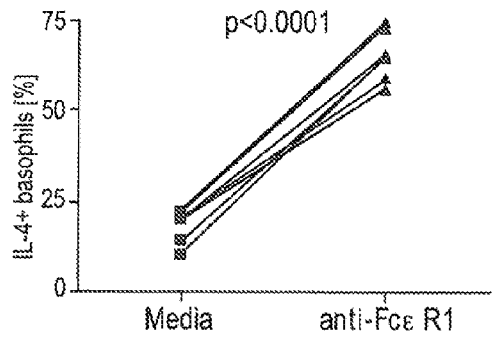
Figure 1E:
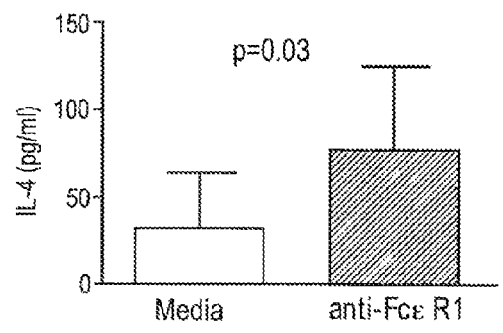

To determine whether anti-FcεRI antibody also activates basophils in vitro, whole blood samples from NOD mice were assessed for basophil IL-4 production by intracellular flow cytometry. Basophils were identified by flow cytometry as CD4−B220−IgE+ cells (FIG. 1C) as this staining strategy has been shown to be specific for basophils (16). Whereas an average of 18% of basophils stained positively for IL-4 at baseline, on average 65% were IL-4+ after incubation with anti-FcεRI (p<0.0001, FIG. 1D). To confirm that anti-FcεRI induces IL-4 release from basophils, IL-4 was measured by ELISA in the supernatants of whole blood samples incubated with media or anti-FcεRI. As seen in FIG. 1E, anti-FcεRI caused significant release of IL-4 from whole blood (unstimulated mean IL-4 concentration 32 pg/ml vs mean 77 pg/ml after anti-FcεRI stimulation, p=0.03). As basophils are the only circulating cells in mice that express anti-FcεRI, this assay confirms that anti-FcεRI antibody induces IL-4 release from basophils.

Example 2

Figure 2A:
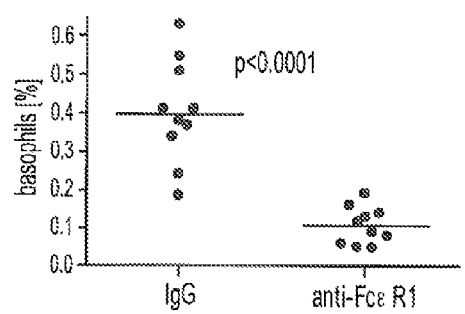
FIG. 2: Effects of anti-FcεRI injections in vivo. Percentages of circulating white blood cells that are basophils (A) and percentages of peritoneal cells that are mast cells (B) in mice one day after intraperitoneal injection of 50 μg of isotype control antibody or anti-FcεRI. (C) Plasma IL-4 concentration as measured by in vivo cytokine capture assay one day after anti-FcεRI or isotype antibody injection. (D) Histamine concentration in plasma 30 minutes after anti-FcεRI or isotype antibody injection. Statistical significance between groups was assessed by the Mann-Whitney test (*<0.05). Joined data from two independent experiments is shown with 5 animals per group and experiment.
Figure 2B:
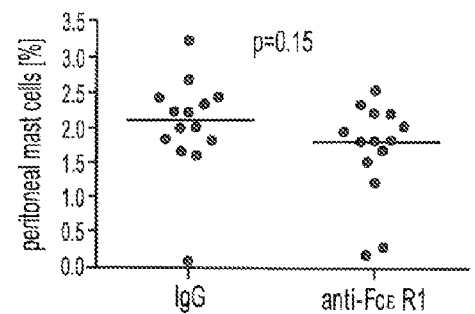

Anti-FcεRI Injections Deplete Basophils and Induce Massive Histamine and IL-4 Release In Vivo As both basophils and mast cells express the FcεRI on their surface, we tested whether treatment with anti-FcεRI antibody depletes either peripheral basophils or peritoneal mast cells by injecting NOD mice with 50 μg of anti-FcεRI and measuring blood basophil and peritoneal mast cell frequencies by flow cytometry. Basophils were identified as CD4−B220−IgE+ cells and peritoneal mast cells were identified as cKit-positive, IgE-positive cells. The frequency of blood cells that were basophils was significantly reduced one day after treatment with anti-FcεRI antibody compared to control animals (median 0.11%, range 0.05-0.19% vs. 0.40%, 0.19-0.63%; FIG. 2A) whereas the frequency of peritoneal mast cells was unchanged (median 1.8%, range 0.2-2.5% vs. 2.1%, 0.1-3.2%, FIG. 2B). This finding is consistent with that of other research groups who have used anti-FcεRI antibody to deplete mice of basophils (21, 27).

Figure 2C:
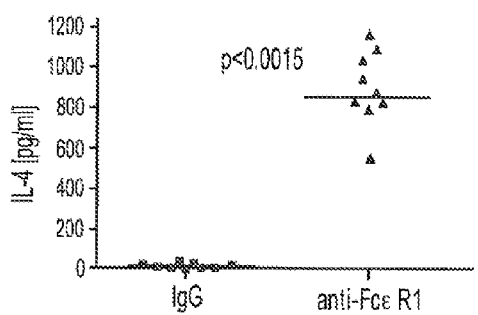
Figure 2D:
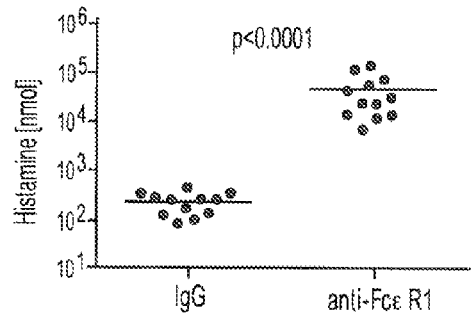

Because aggregation of surface FcεRI activates basophils and mast cells, and since our in vitro studies demonstrated that anti-FcεRI antibody induces basophils and mast cells to release IL-4 and histamine, we tested whether injection of anti-FcεRI antibody increases blood levels of IL-4 and histamine. As seen in FIG. 2C, mice that were injected the previous day with anti-FcεRI had significantly higher frequencies of circulating IL-4, as measured by in vivo cytokine capture assay, compared to isotype antibody treated controls (p=0.0015, median 863 pg/ml, range 0-1173 pg/ml vs. 10 pg/ml, range 0-34 pg/ml). Similarly, histamine, which was measured in peripheral blood obtained 30 minutes after antibody injection due to its very short half-life, was substantially higher in anti-FcεRI-treated mice than in controls. Mice that received anti-FcεRI had a median blood histamine concentration of 28800 nmol (range 7745-137700 nmol) as compared to only 248 pg/ml (range 81-441 pg/ml, p<0.0001, FIG. 2D). As basophils and mast cells are the only cells that contain pre-formed histamine, these results demonstrate that anti-FcεRI antibody injection activates basophils and mast cells in vivo.

Example 3

Anti-FcεRI Treatment Delays the Onset of Diabetes in NOD Mice

To test the hypothesis that chronic activation of basophils and mast cells protects against autoimmune diseases, development of Type I diabetes was monitored in NOD mice that were given repeated anti-FcεRI antibody injections.

Figure 3A:
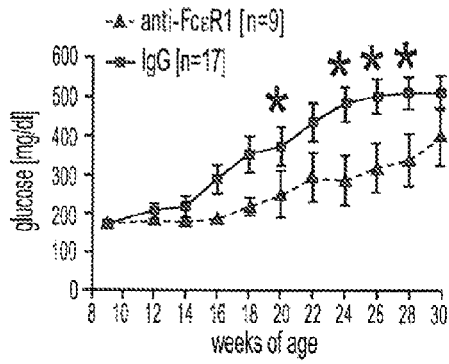
FIG. 3: Treatment with anti-FcεRI delays the onset of diabetes. (A) Mean blood glucose levels and (B) percentages of NOD mice with diabetes during treatment with weekly injections of 50 μg anti-FcεRI (n=9) or IgG control antibody (n=17). (C) Mean total numbers of pancreatic islets from anti-FcεRI or isotype treated mice at 16 weeks of age (9-10 animals per group). Pancreatic islets were classified as non-infiltrated, periinsulitis, and intrainsulitis with less than or more than 50% infiltrated lymphocytes. (D) Blood glucose levels and (E) percentages of diabetic mice that received either weekly injections of 50 μg anti-FcεRI for four weeks or injections of 25 or 50 μg anti-FcεRI twice a week for four weeks (n=8 per group) or isotype controls (n=11). Error bars denote SEM. Statistical significance between groups was assessed by the Mann-Whitney test (*<0.05). Shown are the results from 2-3 independent experiments.
Figure 3B:
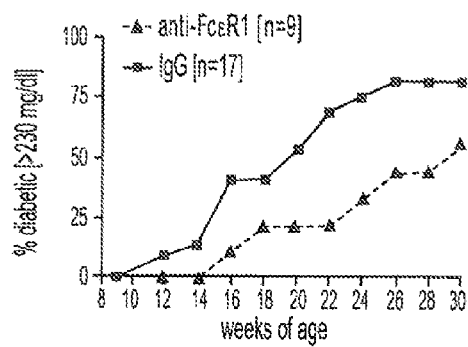
Figure 3C:
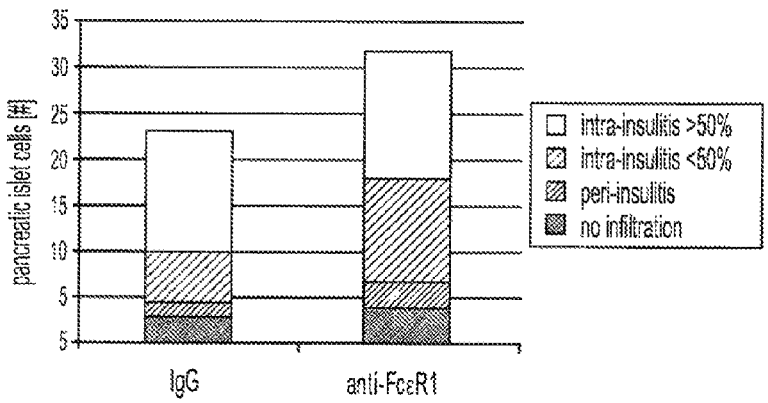

Continuous injections with anti-FcεRI significantly reduced blood glucose concentrations in NOD mice at 20 and 24-28 weeks of age compared to control animals (FIG. 3A) and delayed the onset of diabetes (onset of diabetes in 50% of the animals: IgG group: 20 weeks of age, anti-FcεRI: 30 weeks of age, FIG. 3B). Histological analysis of the pancreas revealed that anti-FcεRI-treated mice had an increased total number of β-islet cells and less lymphocyte infiltration of the pancreatic islets compared to IgG treated mice at 16-weeks of age, although these differences were not statistically significant (FIG. 3C).

Figure 3D:
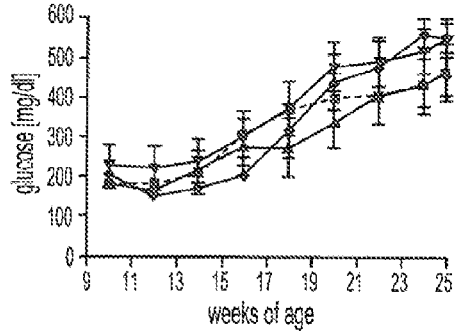
Figure 3E:
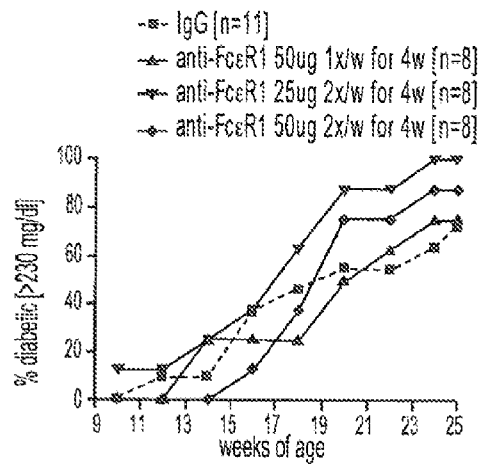

Shorter anti-FcεRI antibody treatment periods from 6-9 weeks of age did not provide a similar protective effect. Neither 4 weekly injections with 50 μg of anti-FcεRI, nor 4 weeks of injections with 25 or 50 μg twice a week decreased blood glucose levels or the frequency of diabetic NOD mice compared to isotype antibody-treated controls (FIGS. 3D and 3E).

Example 4

Figure 4A:
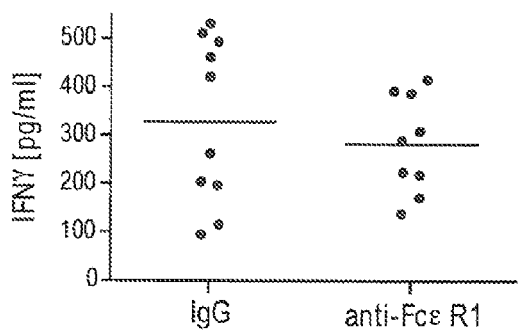
FIG. 4: Cytokine and antibody response after 10 weeks of anti-FcεRI/isotype treatment at 16 weeks of age. (A) IFNγ, (B) IL-4, and (C) IL-5 cytokine production from spleen cells and (D) IFNγ and (E) IL-5 cytokine production from pancreatic lymph node cells in response to anti-CD3/anti-CD28. (F) Frequency of splenic CD4+IFNγ+ and (G) CD8+IFNγ+, as well as (H) CD4+IL-4+ and (I) CD4+IL-17+ T cells in response to anti-CD3/anti-CD28. (J) Plasma levels of insulin-specific IgG1 and (K) IgG2c. Statistical significance between groups was assessed by the Mann-Whitney test. Shown are the results from two independent experiments with a total of 9-10 animals per group.
Figure 4B:
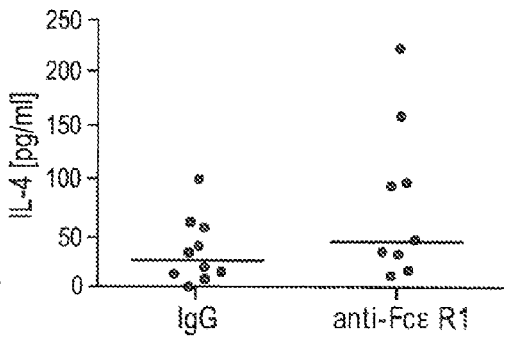
Figure 4C:
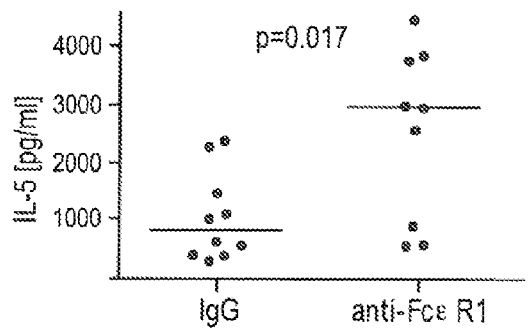
Figure 4D:
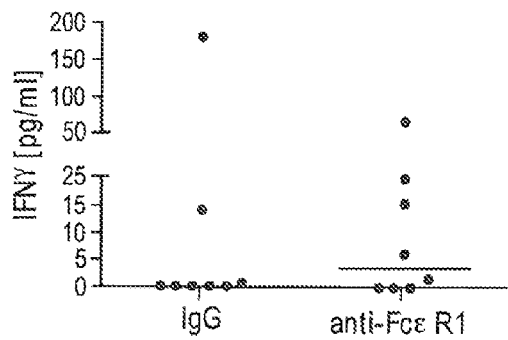
Figure 4E:
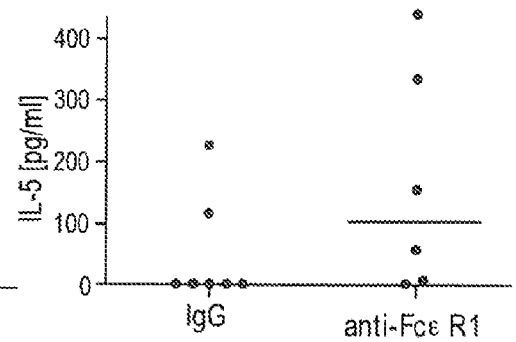

Anti-FcεRI Treatment Induces a Th2 Shift in Antibody, but not Cytokine Production The effect 10 weeks of anti-FcεRI treatment has on cellular cytokine production was evaluated from spleen and pancreatic lymph node cells of 16 week old NOD mice after stimulation with anti-CD3/anti-CD28. IFNγ and IL-4 levels were similar between isotype antibody-injected controls and anti-FcεRI-treated animals (FIGS. 4A and 4B), whereas the concentration of IL-5 was significantly increased in anti-FcεRI-treated mice (FIG. 4C). Pancreatic lymph node cells from anti-FcεRI-injected mice produced more IL-5 and IFNγ in response to anti-CD3/anti-CD28 compared to controls, although these differences did not reach statistical significance (FIGS. 4D and 4E).

Figure 4F:
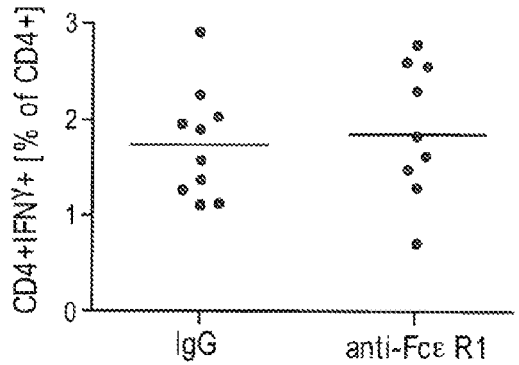
Figure 4G:
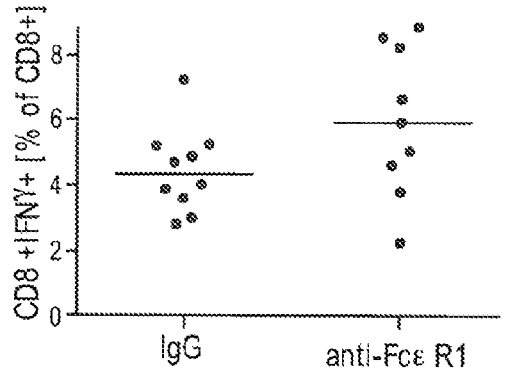
Figure 4H:
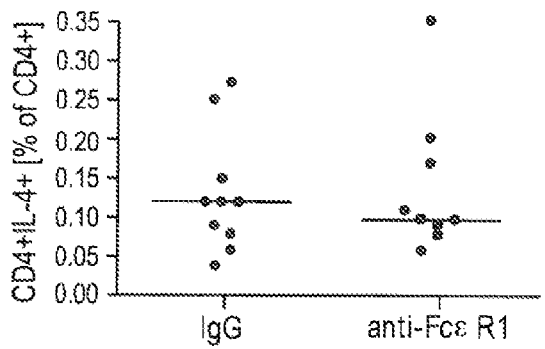
Figure 4I:
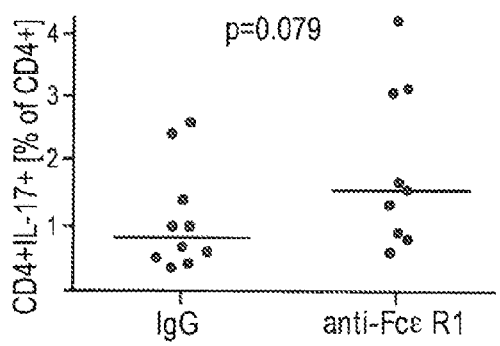

Frequencies of splenic CD4+IFNγ+ T cells and CD8+ IFNγ+ T-cells (FIGS. 4F and 4G) as well as CD4+IL-4+ T-cells (FIG. 4H) after in vitro stimulation with anti-CD3/anti-CD28 were not significantly affected by anti-FcεRI treatment. Frequencies of splenic anti-CD3/anti-CD28 stimulated CD4+IL-17+ T-cells were increased in anti-FcεRI-treated animals compared to controls, though this difference did not reach statistical significance (p=0.079, FIG. 4I).

Figure 4J:
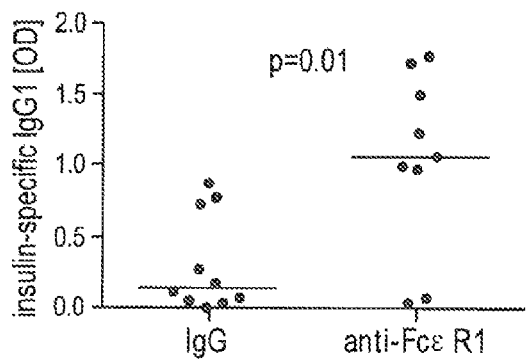
Figure 4K:
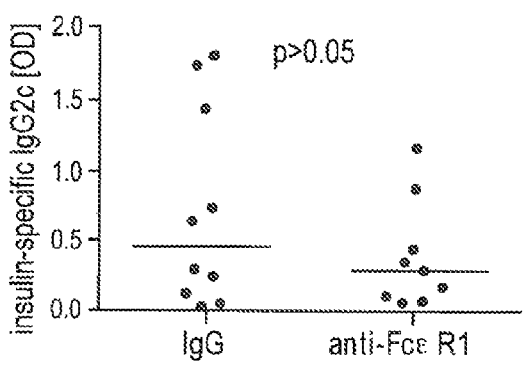

As antigen-specific cellular immune responses are difficult to detect in NOD mice, we tested whether repeated anti-FcεRI antibody injections induce either insulin-specific Th1 (IgG2c) or Th2 (IgG1) associated antibody subsets. Mice that were treated for 10 weeks with anti-FcεRI antibodies had significantly increased levels of insulin-specific IgG1 compared to isotype antibody-injected controls whereas levels of insulin-specific IgG2c were unchanged (FIGS. 4J and 4K).

Example 5

Anti-FcεRI Treatment Induces a Marginal Increase in Regulatory Responses

Frequencies of regulatory T cells and the production of the immunoregulatory cytokine IL-10 were measured from spleen and pancreatic lymph node cells in response to anti-CD3/anti-CD28 after 10 weeks of anti-FcεRI antibody treatment to assess the development of a regulatory immune response.

Figure 5A:
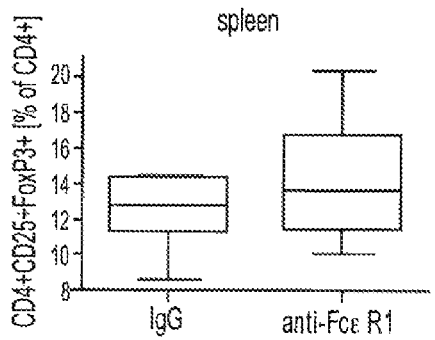
FIG. 5: Frequency of CD4+CD25+FoxP3+ regulatory T cells and IL-10 production after 10 weeks of anti-FcεRI/isotype treatment at 16 weeks of age. (A) Frequency of splenic and (B) pancreatic lymph node CD4+CD25+FoxP3+ regulatory T cells in response to anti-CD3/anti-CD28. (C) Frequency of spontaneous splenic CD8+FoxP3+ regulatory T cells, (D) anti-CD3/anti-CD28 stimulated IL-10+ B-cells, and (E) B220+CD5+CD1d+ regulatory B-cells. (F) IL-10 release from spleen as well as (G) pancreatic lymph node cells in response to anti-CD3/anti-CD28. Statistical significance between groups was assessed by the Mann-Whitney test (spleen: 9-10 animals per group, pancreatic lymph node: 6 animals per group, CD8+ and B-regulatory cells: 4 animals per group). Shown are the results from two independent experiments.
Figure 5B:
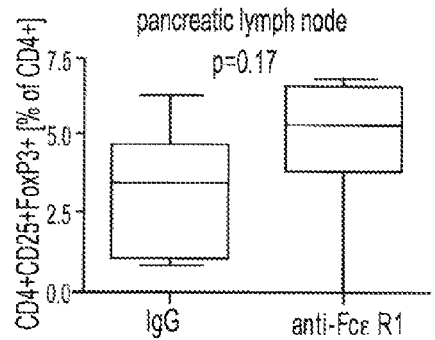
Figure 5C:
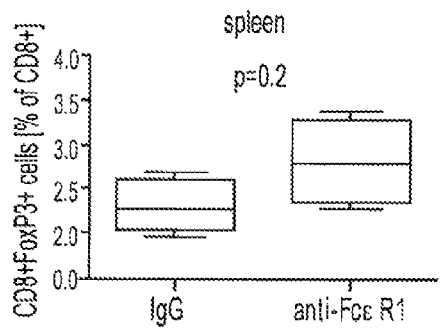
Figure 5D:
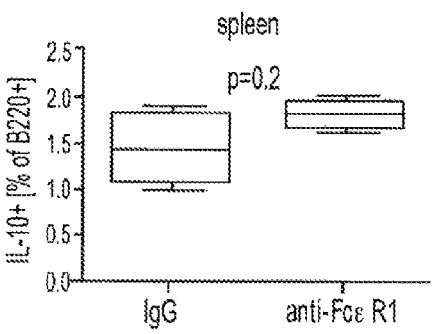
Figure 5E:
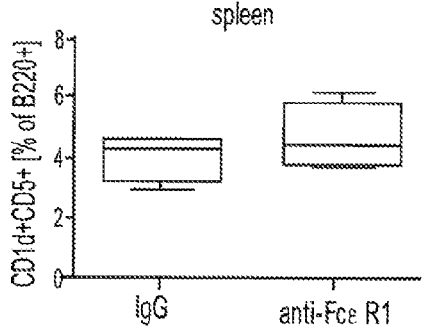
Figure 5F:
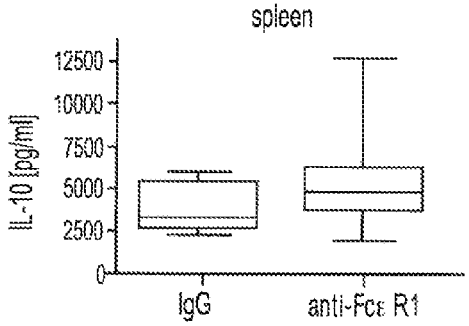
Figure 5G:
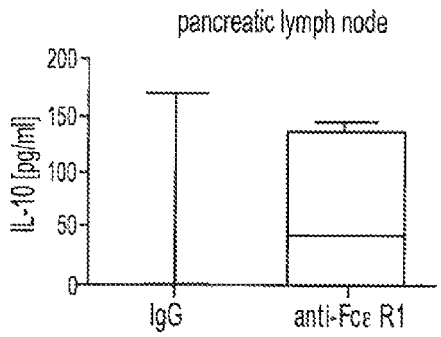

While repeated anti-FcεRI treatment did not substantially alter the percentage of CD4+ T-cells that were CD25+FoxP3+ in the spleen (mean 12.5% in isotype treated mice vs 13.3% in anti-IgE-treated), mean percentages of CD4+CD25+FoxP3+ regulatory T cells in the pancreatic lymph nodes did increase substantially (3% in isotype-treated vs 5.2% in anti-FcεRI treated, FIG. 5B) though this difference did not reach statistical significance (p=0.17). Similarly, percentages of CD8+ spleen cells that were positive for FoxP3+ (FIG. 5C), splenic B-cells that produced IL-10 (FIG. 5D), and splenic B-cells that expressed a regulatory phenotype (B220+CD1d+CD5+, FIG. 5E) were all increased after anti-FcεRI-treatment, though none reached statistical significance. Repeated anti-FcεRI antibody injections also slightly increased splenic (p=0.18, FIG. 5F) and pancreatic lymph node cell (p=0.44, FIG. 5G) IL-10 production in response to anti-CD3/anti-CD28, though again the increases were not statistically significant.

Example 6

Histamine Signaling Through H1 and H2 Receptors is not Necessary for Anti-FcεRI Induced Delay of Type I Diabetes As injection with anti-FcεRI resulted in the release of increased amounts of histamine and as histamine can have immunomodulatory properties, we tested whether blockade of H1 and H2 histamine receptors would prevent anti-FcεRI-mediated delay of diabetes onset in NOD mice.

Cimetidine (an H2 receptor blocker) and fexofenadine (an H1 receptor blocker) were administered by addition to the drinking water of NOD mice from 6 weeks of age to study endpoint at 25 weeks of age at concentrations used by prior investigators (28, 29).

Figure 6A:
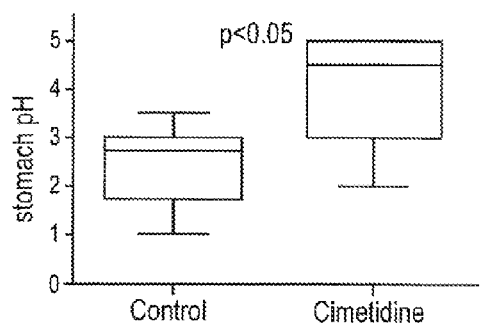
FIG. 6: Histamine receptor blockage does not decrease anti-FcεRI mediated delay of diabetes onset. (A) Stomach pH from animals that were treated for 2 weeks with the Histamine receptor blockers cimetidine and fexofenidine (5 animals per group). (B) Representative pictures of mice that were injected i.v. with toludine blue following challenge with an anti-FcεRI antibody (MAR-I) (left ear) and IgG control (right ear). The bottom mouse was treated with Fexofenidine, a histamine receptor 1 blocker, whereas the top mouse is an untreated control. (C) Blood glucose levels and (D) percentage of diabetic NOD mice that were weekly injected with 50 μg of an anti-FcεRI antibody (MAR-I) or an IgG control antibody and received continuous administration of histamine receptor blockers. Error bars denote SEM. Statistical significance between groups was assessed by the Mann-Whitney test (*<0.05). Shown are the results from two independent experiments.
Figure 6B:
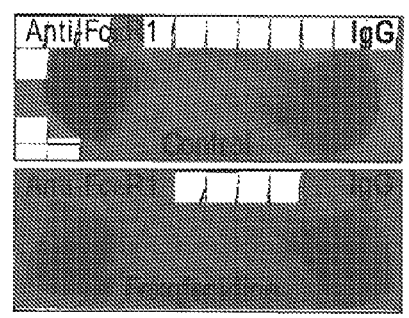

Efficacy of $H_2$-receptor blockade was confirmed by a significant increase in the stomach pH of treated animals compared to controls (FIG. 6A). Blockade of $H_1$-receptors was confirmed by evaluating changes in vascular leak in response to intradermal anti-FcεRI injection. To improve visualization of vascular leakage in the ear, NOD mice were given intravenous injections of toluidine blue. Control NOD mice exhibited substantial local vascular leakage in response to intradermal injection with anti-FcεRI antibody whereas fexofenadine-treated mice did not (FIG. 6B, left ears). Vascular leakage was a specific response to anti-FcεRI antibody, as intradermal injection of control antibody did not induce vascular leakage (FIG. 6B, right ears).

Figure 6C:
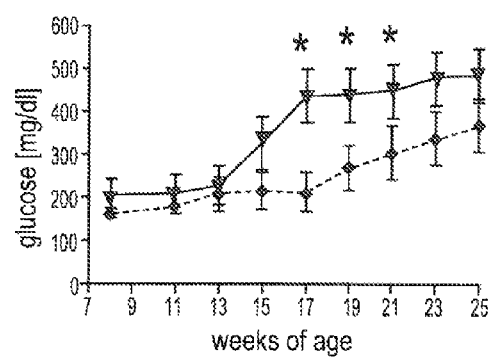
Figure 6D:
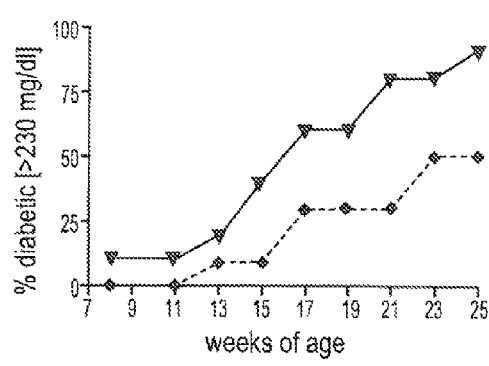

As seen in FIGS. 6C and 6D, continuous histamine receptor blockade did not negate the protective effect of anti-FcεRI antibody treatment on the development of diabetes in NOD mice. Anti-FcεRI antibody treatment during histamine receptor blockade resulted in significantly reduced blood glucose levels at 17-21 weeks of age (FIG. 6C) and delayed the onset of diabetes compared to control animals (onset of diabetes in 50% of the animals: IgG isotype group: 17 weeks of age, anti-FcεRI antibody group: 23 weeks of age, FIG. 6D).

Example 7

Efficacy of Anti-FcεRI Antibody-Mediated Protection is Reduced in the Absence of IL-4

As anti-FcεRI antibody injection increased in vivo IL-4 levels and as IL-4 can counterbalance pathogenic Th1 autoimmune responses, we tested whether the protective effect of anti-FcεRI antibody was dependent on IL-4 by treating IL-4-deficient NOD mice with repeated weekly anti-FcεRI injections.

Figure 7A:
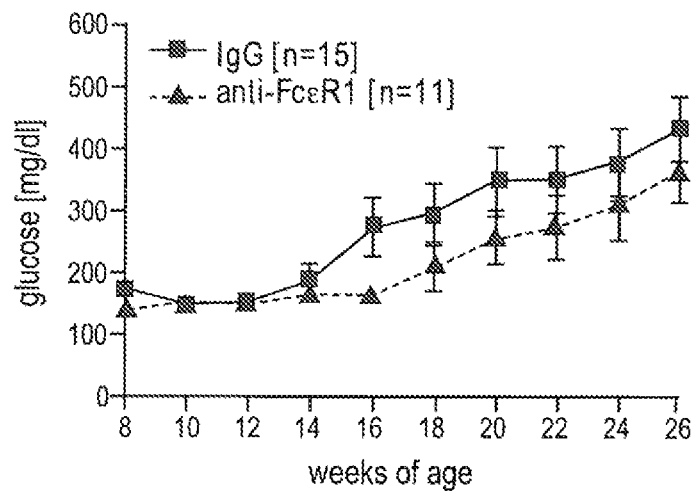
FIG. 7: Deficiency of IL-4 reduces anti-FcεRI mediated protective effect. (A) Blood glucose levels and (B) percentage of diabetic IL-4 deficient NOD mice that were weekly injected with 50 μg of an anti-FcεRI antibody (MAR-I) or an IgG control antibody. Error bars denote SEM. Statistical significance between groups was assessed by the Mann-Whitney test (*<0.05). Shown are the results from four independent experiments.
Figure 7B:
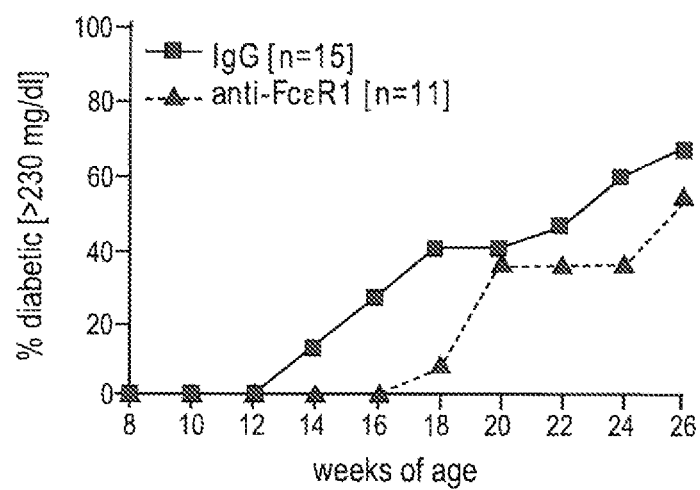

Weekly injections of anti-FcεRI or control IgG were given from 6-20 weeks of age. Although blood glucose levels were reduced in anti-FcεRI-treated IL-4-deficient animals (FIG. 7A) the difference compared to IgG treated animals was less prominent than had been previously observed in immunocompetent NOD mice (FIG. 3A) and did not reach statistical significance. Similarly, protection against overt diabetes, while still present (onset of diabetes in 50% of the animals: isotype antibody group: 24 weeks of age, anti-FcεRI antibody group: 26 weeks of age, FIG. 7B), was substantially less than had been observed in immunocompetent mice (FIG. 3B).

Example 8

Increased Frequency of Anti-FcεRI Administration in NOD Mice Enhances Efficacy

Figure 8:
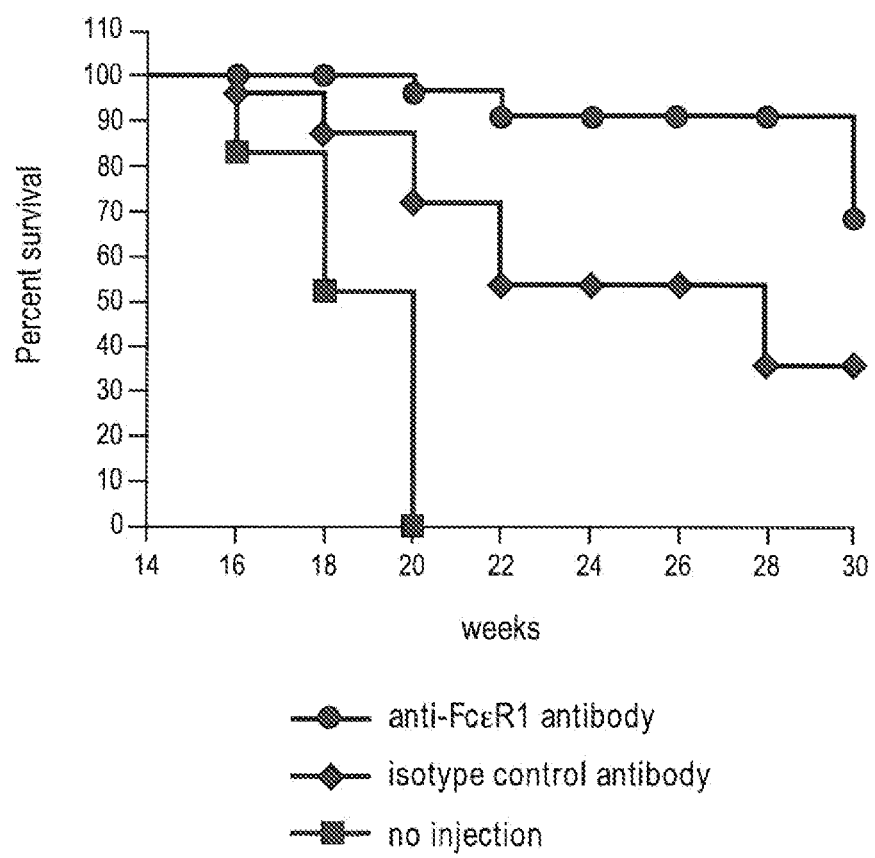
FIG. 8: More frequent administration of anti-FcεRI enhances survival rates in NOD mice even after the development of auto-antibodies. This figure shows the percent survival in female NOD mice given daily i.p. injections of 5 μg anti-FcεRI (top line, circles), isotype control antibody (middle line, diamonds), or no injections (bottom line, squares) for 10 days starting at 12 weeks of age. n=5 per group.

In an effort to improve the efficacy of anti-FcεRI antibody treatment in the NOD mouse model, we tested a more intensive and front-loaded regimen of anti-FcεRI therapy given to older NOD mice. Mice were administered 5 μg of anti-FcεRI antibody daily for 10 consecutive days. Rather than initiating the anti-FcεRI therapy at 6 weeks, as in the previous studies, anti-FcεRI antibody was not initiated until 12 weeks of age. As seen in FIG. 8, administration of 5 μg of anti-FcεRI antibody daily for 10 consecutive days resulted in almost complete protection from type 1 diabetes in NOD mice up to 28 weeks of age. Furthermore, this observed protection in NOD mice is particularly impressive given that the anti-FcεRI injections were not initiated until 12 weeks of age—a time point at which NOD mice routinely have ongoing inflammation in their pancreatic islets. Thus, this more intensive regimen appears more effective than the prior dosing strategy (10 weekly i.p. injections of 50 μg anti-FcεRI antibody) and shows that anti-FcεRI therapy can be used to treat active autoimmune disease.

Discussion:

This study demonstrates that repeated anti-FcεRI therapy can be used to treat Type 1 diabetes in an art-recognized mouse model. Continuous administration of anti-FcεRI antibody reduced the incidence of diabetes in NOD mice by ~50% compared to controls and was associated with increased total numbers of pancreatic β-islet cells. Increasing the frequency of anti-FcεRI antibody administration improves the efficacy of treatment and dramatically increases the survival rate of NOD mice with active disease. The protective effects were more pronounced following chronic treatment with anti-FcεRI antibody, whereas shorter treatment regimens for 4 weeks did not result in appreciable disease protection.

In vitro and in vivo assays showed that anti-FcεRI antibody activates basophils and mast cells and greatly increases circulating levels of histamine and IL-4. We suspect that the bulk of the IL-4 release was due to basophil activation, since basophils are the only cells known to store large quantities of pre-formed IL-4 (30), are major contributors of IL-4 in helminth infections and allergic diseases (17, 19, 31), and have been demonstrated to release more IL-4 on a per cell basis than other cell types (32, 33). To our knowledge this is the first demonstration that chronic activation of basophils and mast cells is associated with protection against autoimmunity.

Although continuous treatment with anti-FcεRI antibody did not result in a clear Th2 shift in cytokine production, as measured from spleen and pancreatic lymph node cells, increases in insulin-specific IgG1 revealed a type 2 (Th2) immune shift in antibody production. Increased serum levels of IL-4 following anti-FcεRI antibody treatment suggest that this type 2 immune shift in antibody responses may have been driven by IL-4 released from innate cells activated by antibody rather than T-cells. This type 2 immune shift in insulin-specific antibody isotypes is similar to that observed when NOD mice are infected with the filarial nematode *Litomosoides sigmodontis* (8), an intervention that also results in protection against diabetes.

While histamine signaling through H1 and H2 receptors does not appear necessary for protection, as treatment with H1 and H2 receptor blockers did not attenuate the protective effects of anti-FcεRI injections, results obtained with IL-4 deficient NOD mice demonstrate that IL-4 is partly responsible for therapeutic benefit. The finding that IL-4 protects against autoimmune disease is consistent with prior studies. In NOD mice, systemic administration of IL-4 (34, 35), expression of IL-4 by pancreatic β-islet cells (36), and transfer of IL-4 expressing DCs (37, 38) have been shown to prevent the onset of autoimmune diabetes. An important role for IL-4 in the control of Th1-mediated autoimmune diseases is further suggested by studies that used helminths to prevent autoimmunity. Helminth or helminth antigen induced protection against autoimmune diabetes is associated with the induction of Th2 immune responses (8) and studies in experimental autoimmune encephalitis and trinitrobenzene sulfonic acid (TNBS) induced colitis showed that *Schistosoma* egg administration failed to protect against autoimmunity in mice deficient in STAT6 or depleted of IL-4 (39). Besides counterbalancing Th1 immune responses, FcεRI-induced IL-4 may protect against Th1 driven autoimmune responses by driving the differentiation of classically (Th1 associated) macrophages into an alternative activated phenotype (AAMØ). AAMØ are anti-inflammatory and are known to be more prevalent during helminth infections (40).

In this study, anti-FcεRI antibodies were used to induce IL-4 release by systemically activating basophils and mast cells. An approach that is based on antibody injections to trigger IL-4 release might be easier to transfer to the bedside compared to therapies that consist of injection with cytokines.

Additionally, given that the protective effects of anti-FcεRI therapy were only partially reduced in IL-4-deficient NOD mice, it is likely that IL-4 independent mechanisms may also play a role in anti-FcεRI therapy. These IL-4 independent mechanisms may be directly related to activation of basophils and/or mast cells, or they may be due to induction of negative feedback pathways induced by chronic activation of these cells.

One IL-4-independent mechanism may be the induction of IL-13 release by anti-FcεRI injections as IL-13 has been shown to prevent diabetes onset in NOD mice (41). Both basophils as well as mast cells can produce IL-13 after cross linking of FcεRI. Because IL-13 signals through IL-4Rα it is possible that anti-FcεRI-induced IL-13 assumed some of the functions of IL-4 in IL-4 deficient NOD mice and contributed to anti-FcεRI mediated protection. Evaluating whether IL-13 plays a role in anti-FcεRI mediated protection against autoimmunity will be the subject of future studies. In contrast, the observed non-significant increase of Th17 cells during anti-FcεRI therapy is very unlikely to be a mechanism by which anti-FcεRI injections protect against Type 1 diabetes because Th17 responses are thought to have a role in the induction of Type I diabetes, possibly by conversion of Th17 to Th1 cells that can cause diabetes onset (42-45).

Another IL-4-independent mechanism that may be important is the induction of immunoregulatory networks. By repeatedly activating basophils and mast cells, we replicated the immunological phenotype observed in chronic helminth infections and in allergen immunotherapy. In helminth infections, basophils and mast cells are continuously being activated by parasite antigens through parasite-specific IgE on the surface of these cells (18). In immunotherapy, patients with allergen-specific IgE are repeatedly given injections of allergen to which they have specific IgE, essentially inducing a chronic state of low level basophil and mast cell activation. While the mechanisms by which chronic helminth infections and allergen immunotherapy modulate the immune system are not completely understood, a number of studies show that both augment key regulators of peripheral tolerance such as IL-10 and T-regulatory cells. Indeed, helminth infections shown to protect against autoimmune diseases in animal models have been repeatedly associated with increases of IL-10 and T-regulatory cells (8, 47, 48).

In our study, while not statistically significant, levels of IL-10 production from splenocytes, frequencies of IL-10 producing B cells, and frequencies of regulatory CD1d+CD5+ B cells were all higher in mice receiving anti-FcεRI antibody injections. As one of the hallmarks of autoimmune diseases is the loss of peripheral tolerance (49), it will be important for future studies to more fully evaluate whether anti-FcεRI therapy functions by augmenting peripheral tolerance. In a similar vein, it would be interesting to evaluate whether allergen immunotherapy in allergic patients has had beneficial effects on patients with concurrent autoimmune diseases.

The results of this study suggest that chronic basophil and mast cell activation can be a safe and feasible therapy, particularly if treatment is started with small amounts of anti-FcεRI antibody, or another basophil/mast cell activating agent, followed by a gradual increase in treatment dosage. Such an approach would be similar to allergen immunotherapy, in which the dose of allergen given is gradually increased over time. Allergen immunotherapy induces repeated basophil and mast cell activation and is routinely conducted in the outpatient arena for diseases as benign as allergic rhinitis.

Importantly, unlike conventional therapies for autoimmune diseases which predominantly work by incapacitating specific arms of the immune system, a therapeutic approach based on the induction of chronic basophil and mast cell activation has the potential to induce a therapeutic effect without irreversibly inhibiting any pathways of the immune system.

In conclusion, this study demonstrates that repeated administration of anti-FcεRI antibodies results in activation of basophils and mast cells and protection against Type 1 diabetes in NOD mice by a mechanism that is partially dependent on IL-4. Given the feasibility of developing antibodies for use in humans, the results of this study suggest that anti-FcεRI antibodies can be used for treating Th1-mediated autoimmune diseases, including, but not limited to, type 1 insulin-dependent diabetes mellitus, scleroderma, multiple sclerosis, posterior uveitis, Crohn's disease, inflammatory bowel disease, and rheumatoid arthritis.

Unless otherwise defined, all technical and scientific terms used herein have the same meaning as commonly understood by one of ordinary skill in the art. In case of conflict, the present specification, including definitions, will control. It will be readily apparent to one of ordinary skill in the relevant arts that other suitable modifications and adaptations to the methods and applications described herein are obvious and may be made without departing from the scope of the invention or any embodiment thereof. In addition, the materials, methods, and examples are illustrative only and not intended to be limiting. All patents, patent applications, and published references cited herein are hereby incorporated by reference in their entirety.

REFERENCES

[1] E. I. Benchimol, K. J. Fortinsky, P. Gozdyra, M. Van den Heuvel, J. Van Limbergen, and A. M. Griffiths, Epidemiology of pediatric inflammatory bowel disease: A systematic review of international trends. Inflamm Bowel Dis (2010).

[2] E. A. Gale, The rise of childhood type 1 diabetes in the 20th century. Diabetes 51 (2002) 3353-61.

[3] E. Koutsouraki, V. Costa, and S. Baloyannis, Epidemiology of multiple sclerosis in Europe: a review. Int Rev Psychiatry 22 (2010) 2-13.

[4] E. V. Loftus, Jr., Clinical epidemiology of inflammatory bowel disease: Incidence, prevalence, and environmental influences. Gastroenterology 126 (2004) 1504-17.

[5] I. Logan, and C. L. Bowlus, The geoepidemiology of autoimmune intestinal diseases. Autoimmun Rev 9 (2010) A372-8.

[6] P. Onkamo, S. Vaananen, M. Karvonen, and J. Tuomilehto, Worldwide increase in incidence of Type I diabetes—the analysis of the data on published incidence trends. Diabetologia 42 (1999) 1395-403.

[7] D. E. Elliott, R. W. Summers, and J. V. Weinstock, Helminths as governors of immune-mediated inflammation. Int J Parasitol 37 (2007) 457-64.

[8] M. P. Hübner, J. T. Stocker, and E. Mitre, Inhibition of type 1 diabetes in filaria-infected non-obese diabetic mice is associated with a T helper type 2 shift and induction of FoxP3+ regulatory T cells. Immunology 127 (2009) 512-22.

[9] P. Zaccone, O. T. Burton, and A. Cooke, Interplay of parasite-driven immune responses and autoimmunity. Trends Parasitol 24 (2008) 35-42.

[10] A. Lehuen, J. Diana, P. Zaccone, and A. Cooke, Immune cell crosstalk in type 1 diabetes. Nat Rev Immunol 10 (2010) 501-13.

[11] R. W. Summers, D. E. Elliott, J. F. Urban, Jr., R. Thompson, and J. V. Weinstock, *Trichuris suis* therapy in Crohn's disease. Gut 54 (2005) 87-90.

[12] M. J. Allison, A. Pezzia, I. Hasegawa, and E. Gerszten, A case of hookworm infestation in a Precolumbian American. Am J Phys Anthropol 41 (1974) 103-6.

[13] H. Aspöck, H. Auer, and O. Picher, *Trichuris trichiura* eggs in the neolithic glacier mummy from the Alps. Parasitology Today 12 (1996) 255-256.

[14] J. A. Jackson, I. M. Friberg, S. Little, and J. E. Bradley, Review series on helminths, immune modulation and the hygiene hypothesis: immunity against helminths and immunological phenomena in modern human populations: coevolutionary legacies? Immunology 126 (2009) 18-27.

[15] J. V. Weinstock, R. W. Summers, D. E. Elliott, K. Qadir, J. F. Urban, Jr., and R. Thompson, The possible link between de-worming and the emergence of immunological disease. Lab Clin Med 139 (2002) 334-8.

[16] M. N. Torrero, D. Larson, M. P. Hübner, and E. Mitre, CD200R surface expression as a marker of murine basophil activation. Clin Exp Allergy 39 (2009) 361-9.

[17] E. Mitre, R. T. Taylor, J. Kubofcik, and T. B. Nutman, Parasite antigen-driven basophils are a major source of IL-4 in human filarial infections. J Immunol 172 (2004) 2439-45.

[18] M. N. Torrero, M. P. Hübner, D. Larson, H. Karasuyama, and E. Mitre, Basophils Amplify Type 2 Immune Responses, but Do Not Serve a Protective Role, during Chronic Infection of Mice with the Filarial Nematode *Litomosoides sigmodontis*. J Immunol 185 (2010) 7426-34.

[19] B. Min, M. Prout, J. Hu-L1, J. Zhu, D. Jankovic, E. S. Morgan, J. F. Urban, Jr., A. M. Dvorak, F. D. Finkelman, G. LeGros, and W. E. Paul, Basophils produce IL-4 and accumulate in tissues after infection with a Th2-inducing parasite. J Exp Med 200 (2004) 507-17.

[20] C. Ohnmacht, and D. Voehringer, Basophil effector function and homeostasis during helminth infection. Blood 113 (2009) 2816-25.

[21] J. G. Perrigoue, S. A. Saenz, M. C. Siracusa, E. J. Allenspach, B. C. Taylor, P. R. Giacomin, M. G. Nair, Y. Du, C. Zaph, N. van Rooijen, M. R. Comeau, E. J. Pearce, T. M. Laufer, and D. Artis, MHC class II-dependent basophil-CD4(+) T cell interactions promote T(H)2 cytokine-dependent immunity. Nat Immunol (2009).

[22] A. Finnegan, K. Mikecz, P. Tao, and T. T. Giant, Proteoglycan (aggrecan)-induced arthritis in BALB/c mice is a Th1-type disease regulated by Th2 cytokines. J Immunol 163 (1999) 5383-90.

[23] M. K. Shaw, J. B. Lorens, A. Dhawan, R. DalCanto, H. Y. Tse, A. B. Tran, C. Bonpane, S. L. Eswaran, S. Brocke, N. Sarvetnick, L. Steinman, G. P. Nolan, and C. G. Fathman, Local delivery of interleukin 4 by retrovirus-transduced T lymphocytes ameliorates experimental autoimmune encephalomyelitis. J Exp Med 185 (1997) 1711-4.

[24] A. Mazzoni, H. A. Young, J. H. Spitzer, A. Visintin, and D. M. Segal, Histamine regulates cytokine production in maturing dendritic cells, resulting in altered T cell polarization. J Clin Invest 108 (2001) 1865-73.

[25] C. A. Akdis, and M. Akdis, Mechanisms and treatment of allergic disease in the big picture of regulatory T cells. J Allergy Clin Immunol 123 (2009) 735-46; quiz 747-8.

[26] C. Uermosi, R. R. Beerli, M. Bauer, V. Manolova, K. Dietmeier, R. B. Buser, T. M. Kundig, P. Saudan, and M. F. Bachmann, Mechanisms of allergen-specific desensitization. J Allergy Clin Immunol 126 (2010) 375-83.

[27] C. L. Sokol, G. M. Barton, A. G. Farr, and R. Medzhitov, A mechanism for the initiation of allergen-induced T helper type 2 responses. Nat Immunol 9 (2008) 310-8.

[28] P. M. Hewitt, N. Armstrong, P. Bowrey, M. Cherian, and D. L. Morris, Cimetidine prevents suppression of delayed hypersensitivity in an animal model of haemorrhagic shock. Injury 33 (2002) 673-8.

[29] N. Watanabe, E. Matsuda, A. Masuda, K. Nariai, and T. Shibasaki, The effects of fexofenadine on eosinophilia and systemic anaphylaxis in mice infected with *Trichinella spiralis*. Int Immunopharmacol 4 (2004) 367-75.

[30] B. F. Gibbs, H. Haas, H. H. Wolff, and J. Grabbe, Early IgE-dependent release of IL-4 and IL-13 from leukocytes is restricted to basophils: a comparison with other granulocytes and mononuclear cells. Inflamm Res 49 Suppl 1 (2000) S9-10.

[31] G. Devouassoux, B. Foster, L. M. Scott, D. D. Metcalfe, and C. Prussin, Frequency and characterization of antigen-specific IL-4- and IL-13-producing basophils and T cells in peripheral blood of healthy and asthmatic subjects. J Allergy Clin Immunol 104 (1999) 811-9.

[32] I. Aoki, C. Kinzer, A. Shirai, W. E. Paul, and D. M. Klinman, IgE receptor-positive non-B/non-T cells dominate the production of interleukin 4 and interleukin 6 in immunized mice. Proc Natl Acad Sci USA 92 (1995) 2534-8.

[33] M. Poorafshar, H. Helmby, M. Troye-Blomberg, and L. Hellman, MMCP-8, the first lineage-specific differentiation marker for mouse basophils. Elevated numbers of potent IL-4-producing and MMCP-8-positive cells in spleens of malaria-infected mice. Eur J Immunol 30 (2000) 2660-8.

[34] M. J. Cameron, G. A. Arreaza, P. Zucker, S. W. Chensue, R. M. Strieter, S. Chakrabarti, and T. L. Delovitch, IL-4 prevents insulitis and insulin-dependent diabetes mellitus in nonobese diabetic mice by potentiation of regulatory T helper-2 cell function. J Immunol 159 (1997) 4686-92.

[35] M. J. Rapoport, A. Jaramillo, D. Zipris, A. H. Lazarus, D. V. Serreze, E. H. Leiter, P. Cyopick, J. S. Danska, and T. L. Delovitch, Interleukin 4 reverses T cell proliferative unresponsiveness and prevents the onset of diabetes in nonobese diabetic mice. J Exp Med 178 (1993) 87-99.

[36] R. Mueller, T. Krahl, and N. Sarvetnick, Pancreatic expression of interleukin-4 abrogates insulitis and autoimmune diabetes in nonobese diabetic (NOD) mice. J Exp Med 184 (1996) 1093-9.

[37] R. J. Creusot, S. S. Yaghoubi, K. Kodama, D. N. Dang, V. H. Dang, K. Breckpot, K. Thielemans, S. S. Gambhir, and C. G. Fathman, Tissue-targeted therapy of autoimmune diabetes using dendritic cells transduced to express IL-4 in NOD mice. Clin Immunol 127 (2008) 176-87.

[38] M. Feili-Hariri, D. H. Falkner, A. Gambotto, G. D. Papworth, S. C. Watkins, P. D. Robbins, and P. A. Morel, Dendritic cells transduced to express interleukin-4 prevent diabetes in nonobese diabetic mice with advanced insulitis. Hum Gene Ther 14 (2003) 13-23.

[39] D. E. Elliott, J. L1, A. Blum, A. Metwali, K. Qadir, J. F. Urban, Jr., and J. V. Weinstock, Exposure to schistosome eggs protects mice from TNBS-induced colitis. Am J Physiol Gastrointest Liver Physiol 284 (2003) G385-91.

[40] S. J. Jenkins, and J. E. Allen, Similarity and diversity in macrophage activation by nematodes, trematodes, and cestodes. J Biomed Biotechnol 2010 (2010) 262609.

[41] P. Zaccone, J. Phillips, I. Conget, R. Gomis, K. Haskins, A. Minty, K. Bendtzen, A. Cooke, and F. Nicoletti, Interleukin-13 prevents autoimmune diabetes in NOD mice. Diabetes 48 (1999) 1522-8.

[42] J. A. Emamaullee, J. Davis, S. Merani, C. Toso, J. F. Elliott, A. Thiesen, and A. M. Shapiro, Inhibition of Th17 cells regulates autoimmune diabetes in NOD mice. Diabetes 58 (2009) 1302-11.

[43] D. Bending, H. De La Pena, M. Veldhoen, J. M. Phillips, C. Uyttenhove, B. Stockinger, and A. Cooke, Highly purified Th17 cells from BDC2.5NOD mice convert into Th1-like cells in NOD/SCID recipient mice. J Clin Invest (2009).

[44] A. Cooke, Th17 cells in inflammatory conditions. Rev Diabet Stud 3 (2006) 72-5.

[45] R. Jain, D. M. Tartar, R. K. Gregg, R. D. Divekar, J. J. Bell, H. H. Lee, P. Yu, J. S. Ellis, C. M. Hoeman, C. L. Franklin, and H. Zaghouani, Innocuous IFNgamma induced by adjuvant-free antigen restores normoglycemia in NOD mice through inhibition of IL-17 production. J Exp Med 205 (2008) 207-18.

[46] M. N. Torrero, M. P. Hubner, D. Larson, H. Karasuyama, and E. Mitre, Basophils amplify type 2 immune responses, but do not serve a protective role, during chronic infection of mice with the filarial nematode Litomosoides sigmodntis. J Immunol (in press).

[47] K. A. Saunders, T. Raine, A. Cooke, and C. E. Lawrence, Inhibition of autoimmune type 1 diabetes by gastrointestinal helminth infection. Infect Immun 75 (2007) 397-407.

[48] P. Zaccone, Z. Fehervari, F. M. Jones, S. Sidobre, M. Kronenberg, D. W. Dunne, and A. Cooke, *Schistosoma mansoni* antigens modulate the activity of the innate immune response and prevent onset of type 1 diabetes. Eur J Immunol 33 (2003) 1439-49.

[49] G. P. Lennon, M. Bettini, A. R. Burton, E. Vincent, P. Y. Arnold, P. Santamaria, and D. A. Vignali, T cell islet accumulation in type 1 diabetes is a tightly regulated, cell-autonomous event. Immunity 31 (2009) 643-53.

[50] Kikutani H, and Makino S, The murine autoimmune diabetes model: NOD and related strains. *Adv. Immunol.* 51 (1992) 285-322.

[51] Kinet J P, The high-affinity IgE receptor (FC epsilon RI): from physiology to pathology. Arum Rev Immun. 17 (1999) 931-72.

What is claimed is:

1. A method of treating a Th1-mediated autoimmune disease in a subject, the method comprising administering to the subject an effective amount of an antibody, or antigen-binding fragment thereof, that binds to the Fc epsilon receptor I (FcεRI), thereby treating the Th1-mediated autoimmune disease, and wherein the antibody is administered in an amount sufficient to crosslink the FcεRI on basophils and/or mast cells, thereby activating the basophils and/or mast cells.

2. The method of claim 1, wherein the antibody is a monoclonal antibody.

3. The method of claim 1, wherein the antibody is a chimeric antibody, a humanized antibody, or a human antibody.

4. The method of claim 1, wherein the antibody is an IgG antibody.

5. The method of claim 1, wherein the antibody is an IgE antibody.

6. The method of claim 1, wherein the FcεRI is a human FcεRI.

7. The method of claim 1, wherein the Th1-mediated autoimmune disease is selected from the group consisting of type 1 insulin-dependent diabetes mellitus, scleroderma, multiple sclerosis, posterior uveitis, Crohn's disease, inflammatory bowel disease, and rheumatoid arthritis.

8. The method of claim 1, wherein the subject is a mammal.

9. The method of claim 1, wherein the subject is a human.

10. The method of claim 1, wherein the antibody is administered chronically to the subject.

11. The method of claim 10, wherein the antibody is administered to the subject every week for at least 10 weeks.

12. The method of claim 10, wherein the antibody is administered to the subject one or more times per day for at least five consecutive days.

* * * * *